(12) United States Patent
Haj-Ahmad et al.

(10) Patent No.: US 12,084,650 B2
(45) Date of Patent: Sep. 10, 2024

(54) PRESERVATION OF CELL-FREE NUCLEIC ACIDS IN BIOLOGICAL SAMPLES

(71) Applicant: Norgen Biotek Corp., Thorold (CA)

(72) Inventors: Taha Alexander Haj-Ahmad, St. Catharines (CA); Yousef Haj-Ahmad, St. Catharines (CA)

(73) Assignee: Norgen Biotek Corp., Thorold (CA)

( * ) Notice: Subject to any disclaimer, the term of this patent is extended or adjusted under 35 U.S.C. 154(b) by 0 days.

(21) Appl. No.: 18/136,961

(22) Filed: Apr. 20, 2023

(65) Prior Publication Data

US 2023/0365961 A1 Nov. 16, 2023

Related U.S. Application Data

(62) Division of application No. 16/303,684, filed as application No. PCT/CA2017/050587 on May 16, 2017, now Pat. No. 11,767,522.

(Continued)

(51) Int. Cl.
| | |
|---|---|
| *C12Q 1/6806* | (2018.01) |
| *C11D 1/08* | (2006.01) |
| *C11D 1/10* | (2006.01) |
| *C11D 3/04* | (2006.01) |
| *C11D 3/37* | (2006.01) |
| *C12N 1/04* | (2006.01) |

(Continued)

(52) U.S. Cl.
CPC ............ *C12N 15/1006* (2013.01); *C11D 1/08* (2013.01); *C11D 1/10* (2013.01); *C11D 3/046* (2013.01); *C11D 3/37* (2013.01); *C12N 1/04* (2013.01); *C12Q 1/6806* (2013.01); *C12N 9/99* (2013.01)

(58) Field of Classification Search
None
See application file for complete search history.

(56) References Cited

U.S. PATENT DOCUMENTS

| 4,268,406 A | 5/1981 | O'Brien et al. |
| 5,455,344 A | 10/1995 | Harper et al. |

(Continued)

FOREIGN PATENT DOCUMENTS

| CN | 102732503 A | 10/2012 |
| CN | 102743503 A | 10/2012 |

(Continued)

OTHER PUBLICATIONS

Ahn, S. et al., "Comparison of Improvacuter EDTA Tube with BD Vacutainer EDTA Tube for Routine Hematological Analysis: Clinical Significance of Differences, Stability Study, and Effects of K2 and K3 EDTA", Journal of Laboratory Medicine and Quality Assurance 2016; 38, Apr. 5, 2016, pp. 77-86.

(Continued)

*Primary Examiner* — Erin M. Bowers
(74) *Attorney, Agent, or Firm* — COATS & BENNETT, PLLC

(57) ABSTRACT

Provided is a composition for preserving cell-free nucleic acids and/or cells in a biological sample and methods for use thereof. The composition comprises at least one volume excluding polymer, at least one osmotic agent and at least one enzyme inhibitor. The composition optionally further comprises at least one metabolic inhibitor. Further, provided is a kit comprising the composition, preferably in a blood collection tube, or the components of the composition.

13 Claims, 12 Drawing Sheets

Related U.S. Application Data

(60) Provisional application No. 62/342,667, filed on May 27, 2016.

(51) Int. Cl.
*C12N 15/10* (2006.01)
*C12N 9/99* (2006.01)

(56) References Cited

U.S. PATENT DOCUMENTS

| | | | |
|---|---|---|---|
| 6,383,393 B1* | 5/2002 | Colpan | C12N 15/101 536/25.4 |
| 6,821,789 B2 | 11/2004 | Augello | |
| 7,264,927 B2* | 9/2007 | Nargessi | C12N 15/1017 536/25.4 |
| 7,282,371 B2 | 10/2007 | Helftenbein | |
| 7,686,035 B2 | 3/2010 | Goinski | |
| 9,012,135 B2 | 4/2015 | Haj-Ahmad | |
| 2002/0115089 A1 | 8/2002 | Goldstein et al. | |
| 2004/0038269 A1 | 2/2004 | Bimboim | |
| 2006/0147944 A1 | 7/2006 | Chomczynski | |
| 2007/0021591 A1 | 1/2007 | Movius et al. | |
| 2007/0202511 A1 | 8/2007 | Chen et al. | |
| 2008/0146790 A1 | 6/2008 | Grolz et al. | |
| 2009/0130714 A1 | 5/2009 | Majumder et al. | |
| 2013/0273607 A1 | 10/2013 | O'Connor | |
| 2014/0080112 A1 | 3/2014 | Ryan et al. | |
| 2016/0333339 A1 | 11/2016 | Fischer et al. | |

FOREIGN PATENT DOCUMENTS

| | | |
|---|---|---|
| CN | 104041484 A | 9/2014 |
| CN | 104360086 A | 2/2015 |
| CN | 104830831 A | 8/2015 |
| CN | 105158455 A | 12/2015 |
| CN | 105695447 A | 6/2016 |
| EP | 1391520 A1 | 2/2004 |
| KR | 20140090811 A | 7/2014 |
| WO | 2010096323 A1 | 8/2010 |
| WO | 2013045457 A1 | 4/2013 |
| WO | 2013045458 A1 | 4/2013 |
| WO | 2014146780 A1 | 9/2014 |
| WO | 2014146781 A1 | 9/2014 |
| WO | 2014146782 A1 | 9/2014 |
| WO | 2015140218 A1 | 9/2015 |
| WO | 2016079509 A1 | 5/2016 |

OTHER PUBLICATIONS

Haj-Ahmad, T. "How to Preserve Cell-Free DNA and Prevent Cellular Genomic DNA Contamination in Plasma", Norgen Biotek Corp., Application Note 86, retrieved on: Jul. 11, 2023, retrieved from Internet: https://norgenbiotek.com/liquidbiopsy/plasmaserum pp. 1-3, Norgen Biotek Corporation.

Barra, G. et al., "EDTA-mediated inhibition of DNases protects circulating cell-free DNA from ex vivo degradation in blood samples" Clinical Biochemistry, vol. 48, Issue 15, Oct. 15, 2015, pp. 976-981, Elsevier.

El-Ashram, S. et al., "Nucleic acid protocols: Extraction and optimization", Biotechnology Reports, vol. 12, Dec. 1, 2016, pp. 33-39, Elsevier.

Feng, B. et al., "DNA strand exchange catalyzed by molecular crowding in PEG solutions", Chemical Communications 46:, Aug. 8, 2010, pp. 8231-8233, The Royal Society of Chemistry.

Madhad, V. et al., "The Rapid & Non-Enzymatic isolation of DNA from the Human peripheral whole blood suitable for Genotyping", European Journal of Biotechnology and Bioscience, Jan. 20, 2014, pp. 1-16, EJBB.

Nzytech, "NZY Ribonuclease Inhibitor", nzytech gene & enzymes, V2003, retrieved from Internet: https://www.nzytech.com/en/catalogsearch/result/?q=ribonuclease+inhibitor, [retrieved on Jul. 11, 2023], pp. 1-2.

Spink, C. et al., "Effects of Hydration, Ion Release, and Excluded Volume on the Melting of Triplex and Duplex DNA", Biochemistry, vol. 38, No. 1, Dec. 11, 1998, pp. 496-508, ACS Publications.

Stipanuk, M. et al., "Biochemical, Physiological, and Molecular Aspects of Human Nutrition", Third Edition, Chapters 34 and 35, Jun. 2018, pp. 759-800, Elsevier Saunders.

Yang, W. "Nucleases: Diversity of Structure, Function and Mechanism", HHA Public Access, Q Rev Biophys, Jan. 4, 2019, pp. 1-110, National Library of Medicine.

Haj-Ahmad, T. et al., "Assessing the Effect of Simulated Shipping on Cell-Free DNA in Blood Collected in Norgen, Streck and EDTA Tubes", Application Note 87, DNA Sample Preparation, retrieved from the Internet: https://horgenbiotek.com/sites/default/files/resources/App-Note-87-Cell-Free-DNA-Preservative-Shaking-Study.pdf, [retrieved on: Jul. 11, 2023], pp. 1-2.

Norgen Biotek Corp., "Product Flyer for the cf-DNA/cf-RNA Presevative Tubes", retrieved from the Internet: https://norgenbiotek.com/sites/default/files/resources/App-Note-86-Cell-Free-DNA-Preservative-Shipping-Study_0.pdf, [retrieved on: Jul. 11, 2023], pp. 1-4.

Norgen Biotek Corp., "cf-DNA Preservative Tubes, Product # 63950, 63960", 2016, r retrieved from Internet: https://norgenbiotek.com/product/cf-dnacf-ma-preservative-tubes, [retrieved on: Jul. 11, 2023], pp. 1-3.

Cold Spring Harbor Protocols, "Phosphate-buffered saline (PBS)", retrieved from Internet: https://cshprotocols.cshlp.org/content/2006/1/pdb.rec8247nternet:, [retrieved on: Apr. 18, 2023], 2006, pp. 1.

Burzlauer, N. "Declaration of Nadine Burzlauer", Affidavit, Apr. 27, 2023, pp. 1-8, Qiagen GmbH.

Lever, A. et al., "A modular method for the extraction of DNA and RNA, and the separation of DNA pools from diverse environmental sample types", Sec. Extreme Microbiology, vol. 6, Article 476, May 19, 2015, pp. 1-25, Frontiers in Microbiology.

Norgen Biotek Corp. "Safety Data Sheet for the cf-DNA/cf-RNA Preservative", Product code 63900, retrieved from Internet: https://norgenbiotek.com/sites/default/files/resources/63950_63960_Dx63950_SDS.pdf, [retrieved on: Sep. 29, 2017], pp. 1-9.

Norgen Biotek Corp. "Patents screenshot", retrieved from Internet: https://norgenbiotek.com/patents, [retrieved on: Apr. 7, 2023], pp. 1-2.

McLarty, LJ, Yeh CH. 2015. Circulating Cell-Free DNA: The Blood Biopsy in Cancer Management. MOJ Cell Science & Report 2[2]:00021.

Lo Ym et al. Presence of fetal DNA in maternal plasma and serum. Lancet 1997; 350: 485-487.

Everett TR, Chitty LS. Cell-free fetal DNA: the new tool in fetal medicine. Ultrasound Obstet Gynecol 2015; 45: 499-507.

Lun FM, et al. Microfluidics digital PCR reveals a higher than expected fraction of fetal DNA in maternal plasma. Clin Chem 2008; 54: 1664-1672.

Norton SE et al. A stabilizing reagent prevents cell-free DNA contamination by cellular DNA in plasma during blood sample storage and shipping as determined by digital PCR. Clinical Biochemistry 46 (2013) 1561-1565.

Williams, C. et al. A high frequency of sequence alterations is due to formalin fixation of archival specimens. American Journal of Pathology, vol. 155, No. 5, Nov. 1999.

Das, K et al., Effects of a novel cell stabilizing reagent on DNA amplification by PCR as compared to traditional cell stabilizing reagents. Acta Histochemica 116 (2014) 55-60.

PAXgene Blood RNA Kit IVD, Sample & Assay Technologies: http://www.qiagen.com/products/catalog/sample-technologies/ma-sample-technologies/total-ma/paxgene-blood-ma-kit-ivd.

PAXgene Blood DNA Kit: Sample & Assay Technologies: http://www.qiagen.com/products/catalog/sample-technologies/dna-sample-technologies/genomic-dna/paxgene-blood-dna-kit.

Banerjee, S, et al., Quantitative recovery of immunoreactive proteins from clinical samples following RNA and DNA isoloation, 2003, BioTechniques 35:450-456.

PDF Document 'Biuret Nov. 25, 2009' from website DTN/The Progressive Farmer at http://www.dtnprogressivefarmer.com/dtnag/view/ag/printablePage.do?ID=BLOG_PRINTABLE_PAGE&bypassCache=true&pageLayout=v4&blogHandle=production

(56) References Cited

OTHER PUBLICATIONS

&blogEntryId=8a82c0bc2504791101252c20bb9701ee&articleTitle=What's+Biruet&editionName-DTNAgFreeSiteOnline, accessed Dec. 16, 2013.

Abdalla et al., "Efficient Preservation and Purification of Blood RNA at Ambient Temperature", Molecular Biology of the Cell, vol. 24, p. 1560, XP009516288 and Annual Meeting of the American Society For Cell Biology (ASCG), New Orleans, Louisiana, USA (Dec. 14-18, 2013).

Gahlawat, A. et. al., "Evaluation of Storage Tubes for Combined Analysis of Circulating Nucleic Acids in Liquid Biopsies", International Journal of Molecular Sciences, Feb. 6, 2019, pp. 1-10.

Paithankar, K.R., et al., "Precipitation of DNA by polyethylene glycol and ethanol", Nucleic Acids Research, Feb. 6, 1991, pp. 1346, vol. 19, No. 6.

Tellez, C., et al., "Method for the characterization of size-exclusion chromatography media for preparative purification of DNA restriction fragments", Biotechnology Techniques 13, Jun. 1, 1999, pp. 395-401.

Tubio, G. et al., Journal of Chromatography B, "Partitioning features of bovine trypsin and alpha-chymotrypsin in polyethyleneglycol-sodium citrate aqueous two-phase systems", 2007, vol. 852, pp. 244-249 (Year: 2007).

Lis et al., Nucleic Acids Res. 2(3): 383-389 (1975).

Bowers et al., Biochim. Biophys. Acta 1774: 1500-1507 (2007).

Kapa Biosystems, Kapa HTP Library Preparation Kit Technical Data Sheet, https://www.utsouthwestern.edu/labs/next-generation-sequencing-core/assets/KAPA_HTP_Library_Preparation_Kit_TDS.pdf, 2013.

\* cited by examiner

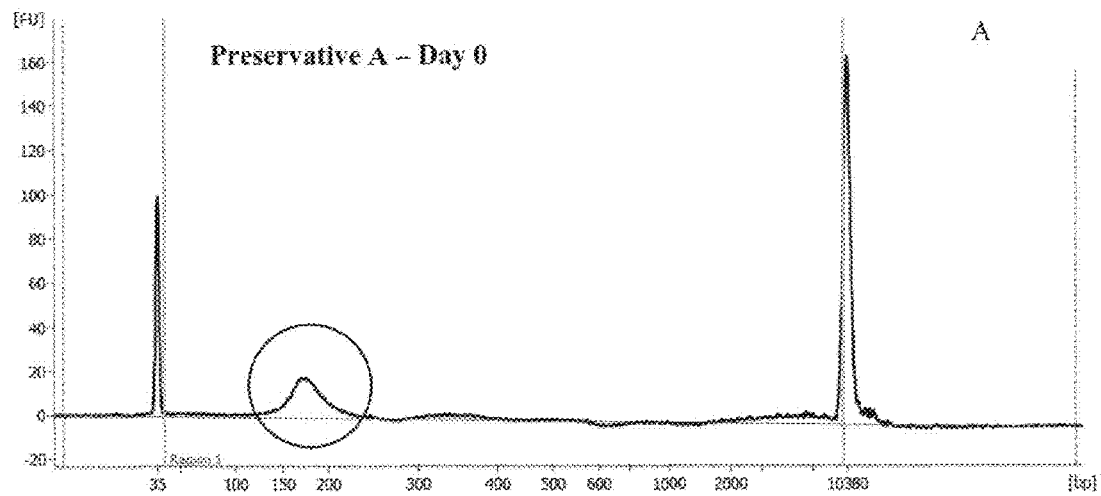
FIGURE 13 – Panel A
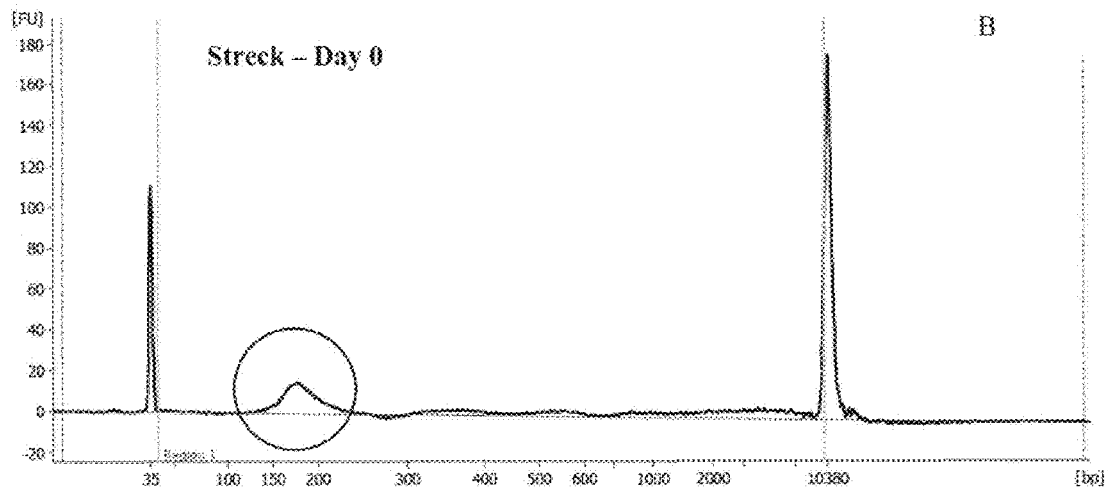
FIGURE 13 – Panel B

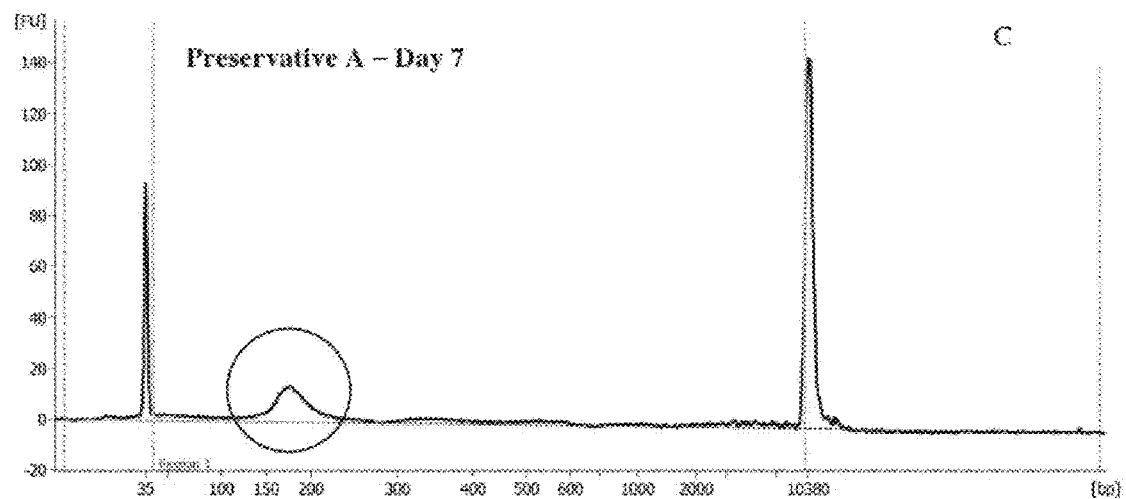
FIGURE 13 – Panel C
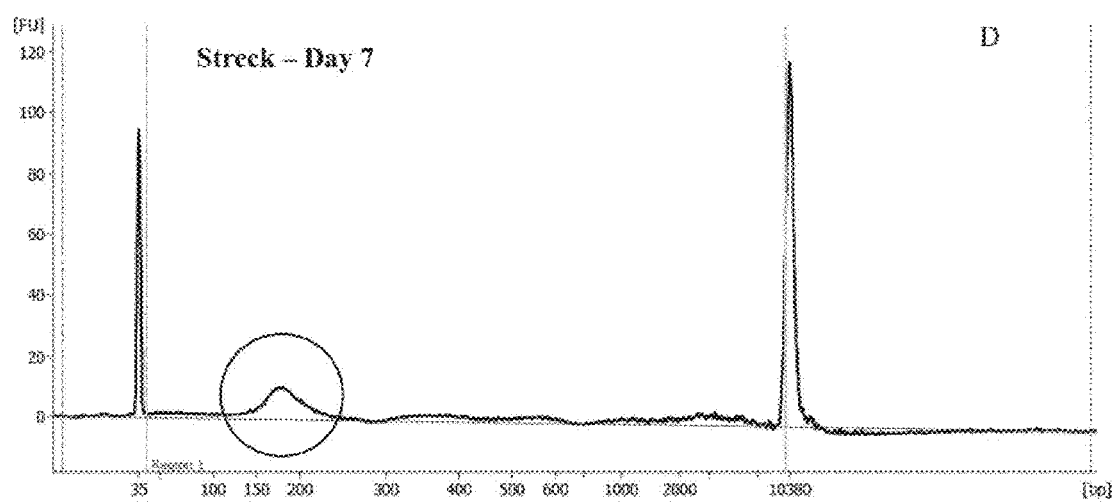
FIGURE 13 – Panel D

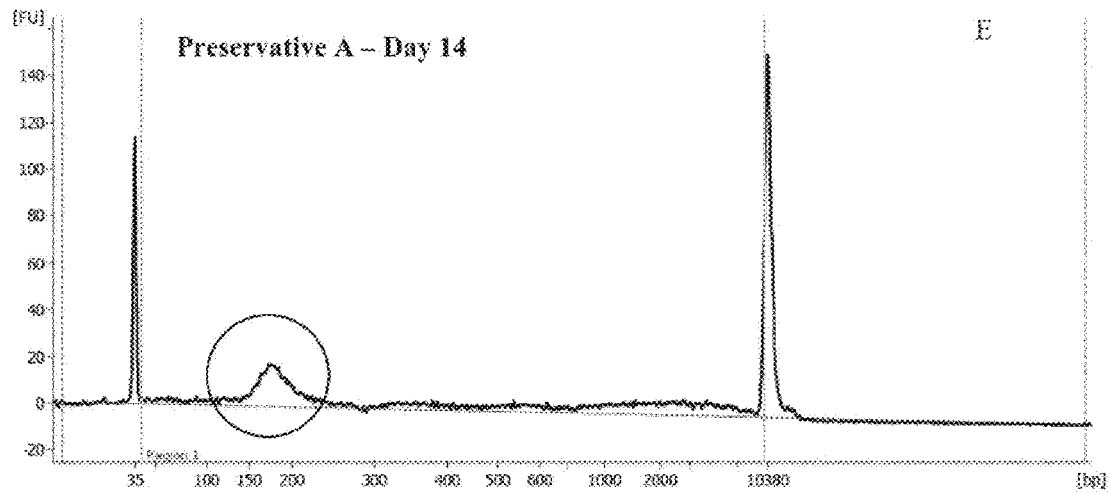
FIGURE 13 – Panel E
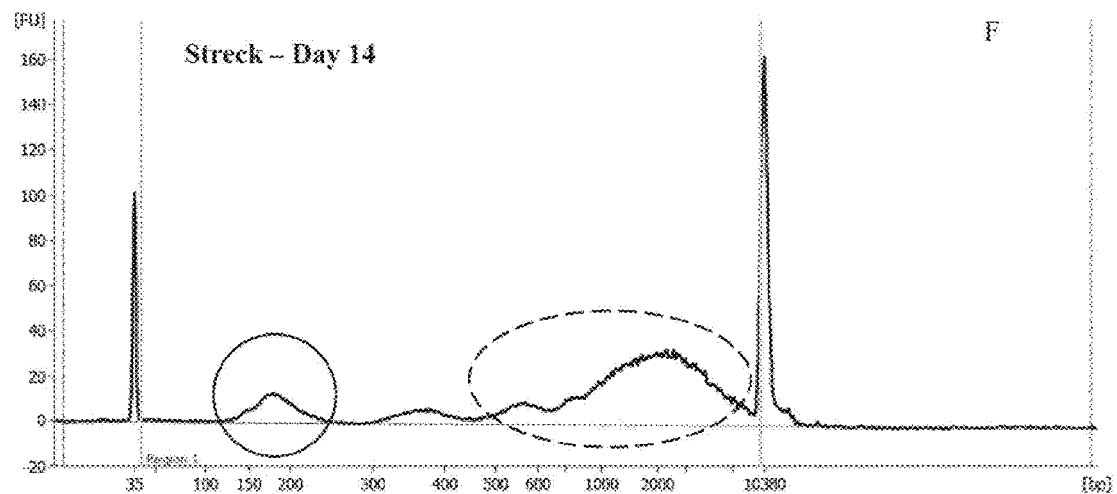
FIGURE 13 – Panel F

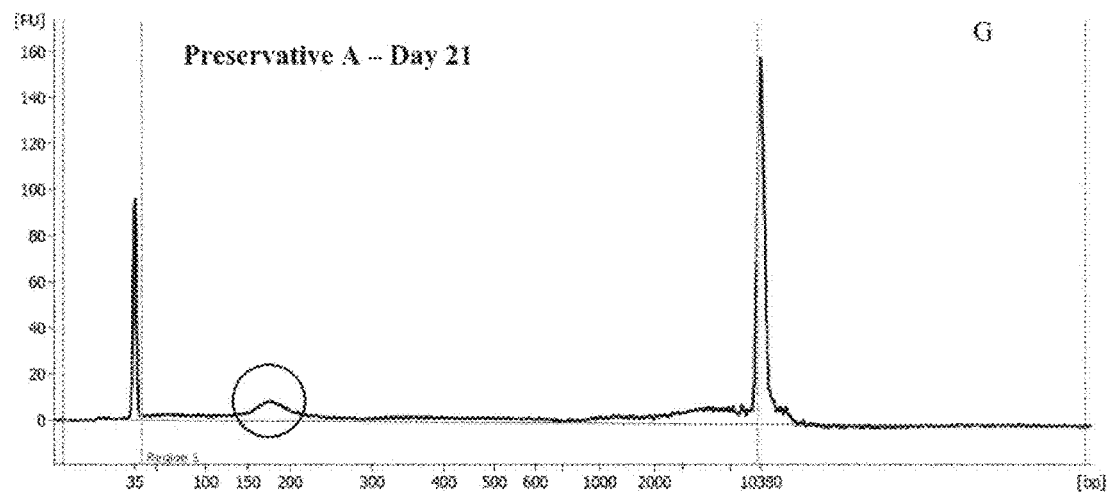
FIGURE 13 – Panel G
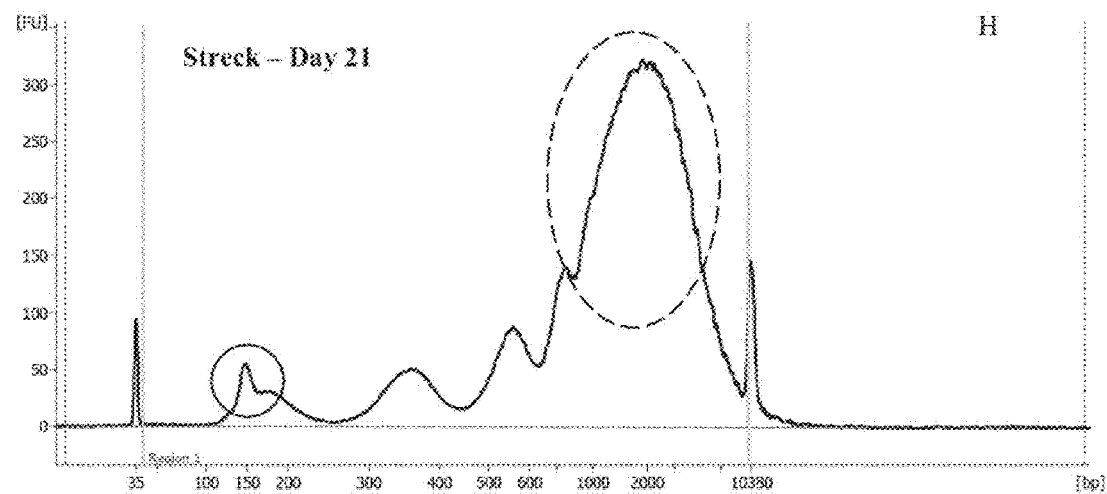
FIGURE 13 – Panel H

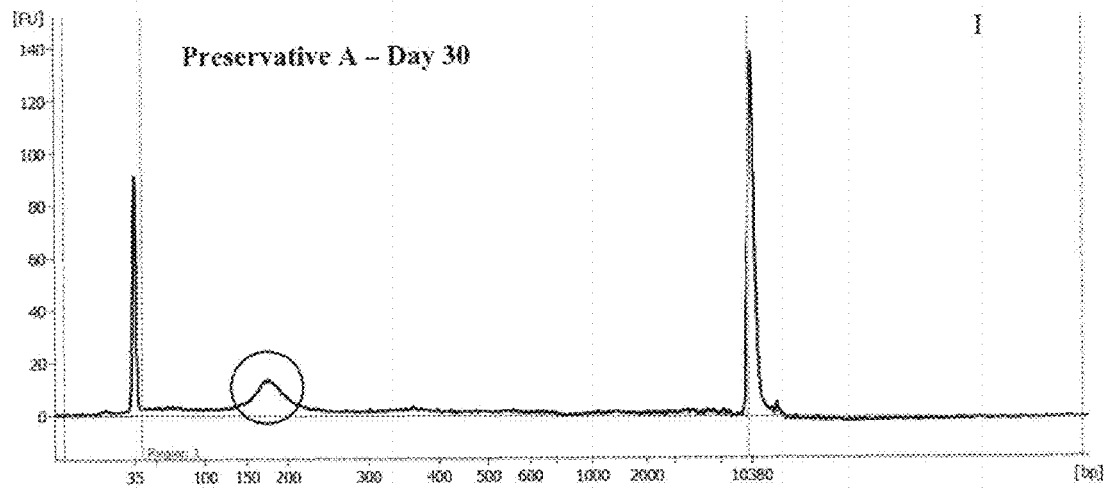
FIGURE 13 – Panel I
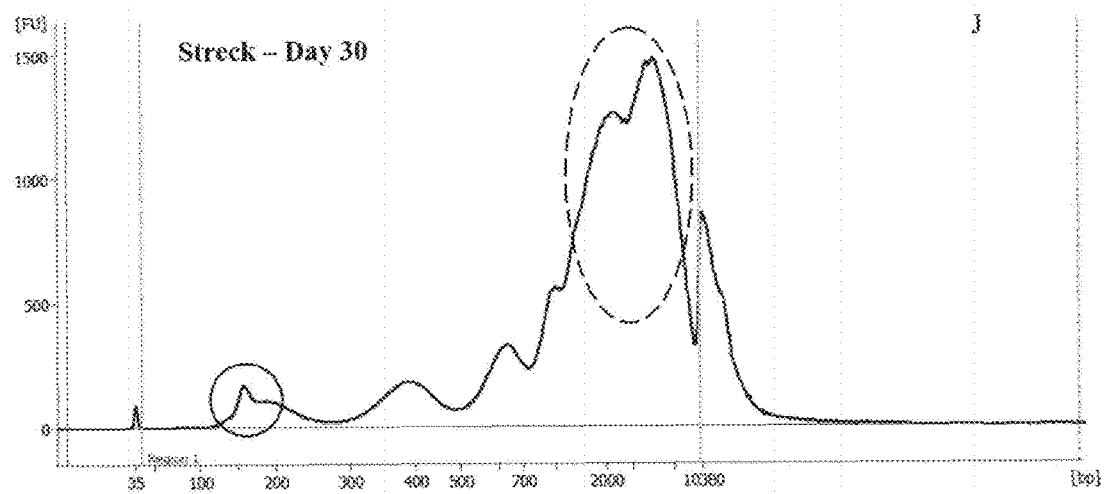
FIGURE 13 – Panel J

PRESERVATION OF CELL-FREE NUCLEIC ACIDS IN BIOLOGICAL SAMPLES

RELATED APPLICATIONS

This application is a divisional of U.S. patent application Ser. No. 16/303,684 filed Nov. 21, 2018, the subject matter of which is incorporated by reference herein in its entirety.

FIELD OF INVENTION

The present invention relates to compositions, methods and kits for the preservation of cell-free nucleic acids in biological samples, and in particular, cell-free DNA isolated from blood or plasma samples.

BACKGROUND

It is well known that cell-free DNA (cfDNA) can be found circulating in the bloodstream. cfDNA can be shed into the bloodstream via active release of newly synthesized nucleic acids, or can result from necrotic and/or apoptotic cell death. The cfDNA fragments are generally less than 200 bp in size (McLarty L J, Yeh C H. 2015. *Circulating Cell-Free DNA: The Blood Biopsy in Cancer Management*. MOJ Cell Science & Report 2[2]: 00021). While cfDNA in the bloodstream is the most commonly studied, cfDNA has also been found in other bodily fluids, including saliva and urine.

Recent research has started to focus on the use of cfDNA in non-invasive diagnostic applications. Elevated concentrations of cfDNA has been found in cancer patients and tumour-specific cfDNA is associated with a number of different cancers, including hematological, colorectal, pancreatic, skin, head-and-neck, lung, breast, gastric, prostate and cervix (McLarty et al. (2015). There is strong evidence that cfDNA can be used as a non-invasive biomarker to diagnose cancer, to monitor disease progression and to monitor treatment response in some individuals.

Additionally, there is interest in the use of cfDNA in applications for non-invasive prenatal testing (NIPT) as cell-free fetal DNA has been found in maternal plasma (Lo Y M et al. *Presence of fetal DNA in maternal plasma and serum*. Lancet 1997; 350: 485-487). Researchers are currently investigating the use of cell-free fetal DNA for fetal sex determination, fetal Rhesus D (RhD) genotyping in RhD-negative mothers, and for the diagnosis of some genetic conditions such as achondroplasia and aneuploidy (Everett T R, Chitty L S. *Cell-free fetal DNA: the new tool in fetal medicine*. Ultrasound Obstet Gynecol 2015; 45: 499-507).

A challenge with the use of cfDNA (such as plasma cfDNA) in diagnostic applications is the detection of the cfDNAs of interest as they are present in very low amounts. For example, in pregnant women, the majority of plasma cfDNA is maternal, with only approximately 10% of the cfDNA constituting cell-free fetal DNA (Lunn F M, Chiu R W, Allen Chan K C, Yeung Leung T, Kin Lau T, Denis Lo Y M. Microfluidics digital PCR reveals a higher than expected fraction of fetal DNA in maternal plasma. Clin Chem 2008; 54: 1664-1672). Similarly, the amount of tumour-associated plasma cfDNA found in cancer patients is typically less than 10% of total cfDNA (Norton S E et al. *A stabilizing reagent prevents cell-free DNA contamination by cellular DNA in plasma during blood sample storage and shipping as determined by digital PCR*. Clinical Biochemistry 46 (2013) 1561-1565). These numbers correspond to very low amounts, since the average concentration of total circulating cfDNA in healthy individuals is only 10-30 ng/mL.

A further challenge with the use of cfDNA in diagnostic applications is contamination of plasma cfDNA with genomic DNA (e.g. maternal or non-tumour) following sample collection due to the lysis of white blood cells during storage and shipping of the sample and the resultant release of genomic DNA (gDNA) into the plasma fraction. As the amount of total cfDNA found in plasma is already very low, and the amount of cfDNA of interest is only a fraction of the cfDNA present, such a release of gDNA would interfere with detection of the cfDNA of interest in downstream applications.

A common method to prevent gDNA release into the plasma fraction is to collect blood into standard EDTA or sodium citrate tubes, followed by cold storage of the blood samples and preparation of the plasma within 6 hours by centrifugation. Once the plasma is prepared, it must be frozen prior to DNA isolation. A problem with this method, however, is that most blood collection sites do not have the required equipment to separate the plasma from the blood samples and therefore must ship the samples to centralized labs or core facilities for plasma processing and subsequent DNA isolation. Furthermore, even if the site does have the ability to prepare the plasma, it must then be kept frozen prior to DNA isolation and downstream diagnostic applications. Thus, the use of standard EDTA or sodium citrate tubes is not ideal or practical for the widespread use of cfDNA for diagnostic applications, particularly for resource-limited labs and areas that lack the required equipment for immediate plasma preparation and for cold storage prior to shipment.

Another method to prevent gDNA release into the plasma fraction is to use chemical stabilizing agents, such as aldehydes (e.g. formaldehyde or glutaraldehyde), which stabilize white blood cells by fixing the cells through cross-linking at the cellular level. There are a number of drawbacks associated with using aldehydes as preservatives for cfDNA, including the formation of DNA-protein and DNA-DNA cross-links, which can negatively affect DNA amplification using PCR, as well as DNA sequencing. Formalin fixation of tissues has been shown to lower the success of PCR amplification due to these issues with cross-linking. Furthermore, it has been demonstrated that when formalin is used to fix tissues, a high frequency of non-reproducible sequence alterations can be detected during direct sequencing. In one study, it was found that up to one mutation artifact per 500 bases was recorded (Williams C et al. *A high frequency of sequence alterations is due to formalin fixation of archival specimens*. American Journal of Pathology, Vol. 155, No. 5, November 1999) in formalin-fixed tissues. In addition, formaldehyde and glutaraldehyde are known to cause damage to DNA in clinical samples (Das K, Fernando M R, Basiaga S, Wigginton S M, Williams T. *Effects of a novel cell stabilizing reagent on DNA amplification by PCR as compared to traditional cell stabilizing reagents*. Acta Histochemica 116 (2014) 55-60). Therefore, while aldehydes can be successfully used as a cell preservative, they have negative effects on downstream analysis and this may interfere with the detection of low abundance cfDNA in plasma samples.

SUMMARY OF INVENTION

In one aspect, provided is a preservative composition for preserving nucleic acids, and in particular, cell-free nucleic acids in a biological sample. The preservative composition can also be used to reduce cell lysis in the biological sample.

In an embodiment, the preservative composition comprises: at least one volume excluding polymer, wherein the volume excluding polymer is present in an amount of about 10 to about 50% by weight of the preservative composition; at least one osmotic agent, wherein the osmotic agent is present in an amount of about 1 to about 20% by weight of the preservative composition and at least one enzyme inhibitor, wherein the enzyme inhibitor is present in an amount from about 1 to about 30% by weight of the preservative composition.

In a further embodiment, the at least one volume excluding polymer is present in an amount of about 10 to about 40% by weight of the preservative composition. The volume excluding polymer is preferably polyethylene glycol (PEG).

In a further embodiment, the osmotic agent is preferably NaCl. The enzyme inhibitor is preferably EDTA or a citrate.

In a further embodiment, the composition further comprises a metabolic inhibitor, wherein the metabolic inhibitor is present in an amount from about 0.01 to about 10% by weight of the composition. The metabolic inhibitor is preferably, sodium azide.

In another aspect, provided is a method for preserving nucleic acids in a biological sample comprising the steps of providing the disclosed preservative composition and contacting the biological sample with the composition to provide a treated sample.

In another aspect, provided is a method for preserving nucleic acids in a biological sample comprising: contacting the biological sample with, in any order or simultaneously, at least one volume excluding polymer, at least one osmotic agent and at least one enzyme inhibitor to provide a treated sample; wherein the amount of the at least one volume excluding polymer is about 2% to about 10% w/w of the total weight of the treated sample; wherein the amount of the at least one osmotic agent is about 0.2% to about 4% w/w of the total weight of the treated sample; and wherein the amount of the at least one enzyme inhibitor is about 0.2% to about 6% w/w of the total weight of the treated sample.

In another embodiment, the volume excluding polymer is preferably polyethylene glycol (PEG). The osmotic agent is preferably NaCl. The enzyme inhibitor is preferably EDTA or a citrate.

In a further embodiment, the composition further comprises a metabolic inhibitor and wherein the amount of metabolic inhibitor is about 0.002% to about 2% w/w of the of the total weight of the treated sample.

In a further embodiment, the biological sample is first contacted with the at least one enzyme inhibitor by collecting the biological sample into a container containing the at least one enzyme inhibitor and the at least one volume excluding polymer and the at least one osmotic agent are then added to the container containing the biological sample and the at least one enzyme inhibitor to provide the treated sample. The container can be a blood collection tube.

In the disclosed methods for preserving nucleic acids, the biological sample may be a biological fluid. The biological fluid may be blood, plasma, serum, urine, saliva, stool, breast milk, tears, sweat, cerebral spinal fluid, synovial fluid, semen, vaginal fluid, ascitic fluid, amniotic fluid, or cell culture media. In a further embodiment, the biological fluid is whole blood. The nucleic acid may cell free RNA, cell free DNA or a combination thereof. The cell-free DNA can be isolated from blood and more specifically, the cell-free DNA is cell-free plasma DNA.

In the disclosed methods for preserving nucleic acids, the treated sample can be stored for a period of least 1 day, at least 7 days, at least 14 days, at least 21 days, at least 28 days, or at least 40 days. At least a portion of the storage period can occur at ambient temperature. Following storage, the disclosed methods may further comprise the step of isolating the nucleic acids from the biological sample. The isolated nucleic acids may be used in a downstream analysis, including diagnosing a disease or infection or for monitoring a disease or infection.

In another aspect, provided is a method for preserving cells in a biological sample comprising the steps of: providing the disclosed preservative composition and contacting the biological sample with the composition to provide a treated sample.

In another aspect, provided is a method for preserving cells in a biological sample comprising: contacting the biological sample with, in any order or simultaneously, at least one volume excluding polymer, at least one osmotic agent and at least one enzyme inhibitor to provide a treated sample; wherein the amount of the at least one volume excluding polymer is about 2% to about 10% w/w of the total weight of the treated sample; wherein the amount of the at least one osmotic agent is about 0.2% to about 4% w/w of the total weight of the treated sample; and wherein the amount of the enzyme inhibitor is about 0.2% to about 6% w/w of the total weight of the treated sample.

In an embodiment, the volume excluding polymer is preferably polyethylene glycol (PEG). The osmotic agent is preferably NaCl. The enzyme inhibitor is preferably EDTA or a citrate.

In a further embodiment, the composition further comprises a metabolic inhibitor and wherein the amount of metabolic inhibitor is about 0.002% to about 2% w/w of the of the total weight of the treated sample. The metabolic inhibitor is preferably, sodium azide.

In a further embodiment, the biological sample is first contacted with the at least one enzyme inhibitor by collecting the biological sample into a container containing the at least one enzyme inhibitor and the at least one volume excluding polymer and the at least one osmotic agent are then added to the container containing the biological sample and the enzyme inhibitor to provide the treated sample. The container can be a blood collection tube.

In the disclosed methods for preserving cells, the biological sample may be a biological fluid. The biological fluid may be blood, plasma, serum, urine, saliva, stool, breast milk, tears, sweat, cerebral spinal fluid, synovial fluid, semen, vaginal fluid, ascitic fluid, amniotic fluid, or cell culture media. In a further embodiment, the biological fluid is whole blood. In a further embodiment, the biological fluid may comprise tumour cells.

In the disclosed methods for preserving cells, the treated sample can be stored for a period of at least 1 day, at least 7 days, at least 14 days, at least 21 days, at least 28 days, or at least 40 days. At least a portion of the storage period can occur at ambient temperature.

In another aspect, disclosed is a kit comprising: the disclosed preservative composition and instructions to combine the preservative composition with a biological sample to provide a treated sample. In an embodiment, the biological sample is a blood sample and the kit may further comprise a blood collection tube.

In another aspect, provided is a kit comprising: at least one volume excluding polymer, at least one osmotic agent; and instructions to combine the at least one volume excluding polymer and at least one osmotic agent with a biological sample and at least one enzyme inhibitor, in any order or simultaneously, to provide a treated sample; wherein the amount of the at least one volume excluding polymer is about 2% to about 10% w/w of the total weight of the treated sample; wherein the amount of the at least one osmotic agent is about 0.2% to about 4% w/w of the total weight of the treated sample; and wherein the amount of the at least one enzyme inhibitor is about 0.2% to about 6% w/w of the total weight of the treated sample.

In an embodiment, the volume excluding polymer is preferably PEG. The osmotic agent is preferably NaCl. The enzyme inhibitor is preferably EDTA or a citrate. The at least one volume excluding polymer and the at least one osmotic agent can be provided as individual components or as a composition.

In a further embodiment, the kit further comprises a metabolic inhibitor and wherein the amount of metabolic inhibitor is about 0.002% to about 2% w/w of the of the total weight of the treated sample. The metabolic inhibitor is preferably sodium azide.

In a further embodiment, the biological sample is a blood sample, and the kit further comprises a blood collection tube containing the at least one enzyme inhibitor.

The disclosed kits may be used for the preservation of nucleic acids in the biological sample. The disclosed kits may be used for the preservation of cells in the biological sample.

BRIEF DESCRIPTION OF THE DRAWINGS

FIG. 13, Panels A-J are spectrograms showing the relative amounts of cfDNA (signal peaks at ca. 170-185 bp) and contaminating gDNA (signal peaks at >185 bp) in blood samples, stored for a period of up to 30 days at room temperature. DNA was isolated from blood collected into: a preservative tube containing a preservative composition as disclosed herein (A) or a preservative tube containing a prior art preservative composition (Streck).

DESCRIPTION

Figure 1:
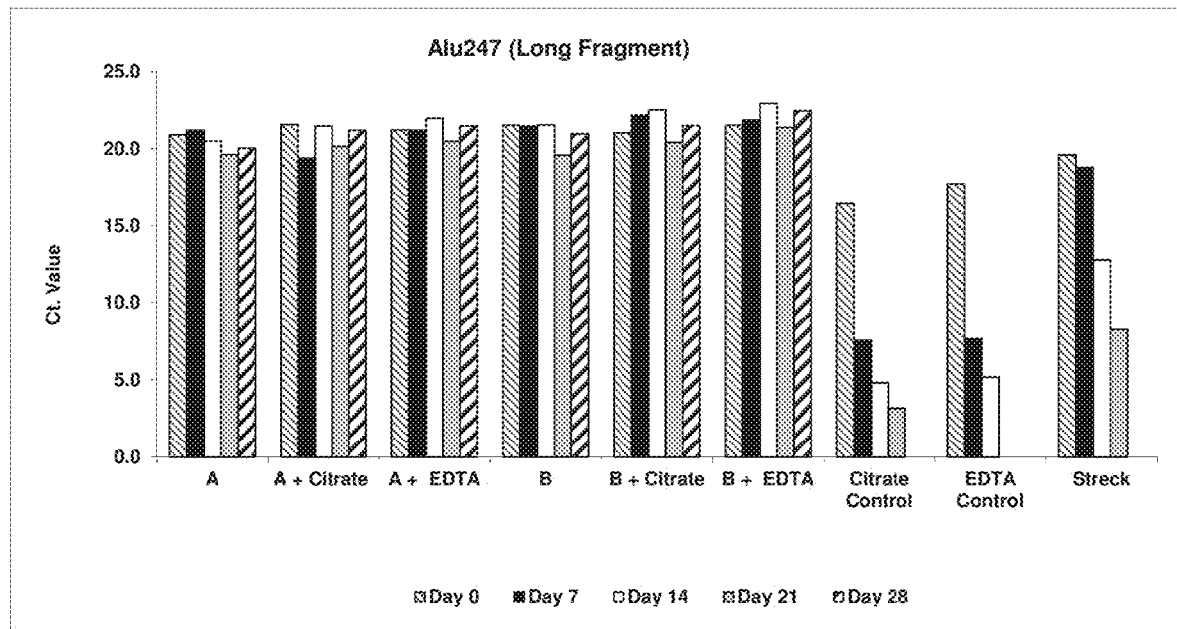
FIG. 1 is a graph showing gDNA contamination in blood samples, stored for a period of up to 28 days, by detecting Alu247 fragments using real time PCR. DNA was isolated from blood collected into: preservative tubes comprising preservative compositions as disclosed herein (A; A+Citrate; A+EDTA; B, B+Citrate; B+EDTA); a preservative tube containing a prior art preservative composition (Streck), a preservative tube containing citrate (Citrate Control) or a preservative tube containing EDTA (EDTA Control).

Provided are compositions, methods and kits that can be used to preserve nucleic acids and/or cells found in biological samples. As used herein, the term "nucleic acid" includes both ribonucleic acid (RNA) and deoxyribonucleic acid (DNA) and further includes RNA and/or DNA, which is linear or branched, single or double stranded or fragments thereof. In particular, the nucleic acids may be cell-free DNA (cfDNA), cell-free RNA (cfRNA) or any combination thereof. The biological sample, comprising the nucleic acids to be preserved, may be any biological fluid, and in particular, may be blood. More particularly, the cell-free nucleic acids are located within plasma.

When biological samples are treated with the preservative composition as disclosed herein, the nucleic acids found in the biological samples can be preserved as compared to untreated biological samples. The preservative composition can help reduce or prevent degradation of nucleic acids of interest in the biological sample and can also help prevent contamination of the nucleic acids of interest with gDNA, as a consequence of cell lysis. Therefore, the preservative composition can help to maintain the nucleic acid profile—and in particular, the cell-free nucleic acid profile—of the sample, even after extended storage. For example, the cell-free nucleic acids found within the biological sample may be afforded protection from contamination with cellular gDNA as treatment with the preservative composition can help to reduce or prevent cell lysis in the biological sample. Further, by preventing or reducing cell lysis in the biological sample, the release of nucleases may also be minimized and as such, nucleic acid degradation may also be minimized. Thus, the benefits of using the disclosed preservative composition for nucleic acid preservation in a biological sample may be two-fold. The cell-free nucleic acids found within the biological sample may be: 1) afforded protection from degradation; and 2) afforded protection from contamination with cellular gDNA by stabilizing cells present in the sample and thereby minimizing the release of gDNA from the cells due to cell lysis. As the disclosed preservative composition can prevent or reduce cell lysis in a biological sample, the composition can also be used to preserve cells contained in a biological sample, such as white blood cells and circulating tumour cells.

Treatment of biological samples with the disclosed preservative composition has been found to facilitate storage of the samples for extended periods without refrigeration prior to sample processing and subsequent nucleic acid isolation. Accordingly, use of the preservative composition as disclosed, may be beneficial for resource limited settings that lack the equipment or resources for the immediate processing and/or cold storage of collected samples. As shown in the Examples, nucleic acids isolated from biological samples treated using the disclosed preservative composition—even without refrigeration for 28 days or more—were found to have substantially maintained their cfDNA profiles. Further, as shown in the Examples, contamination of the cfDNA with gDNA was minimized during storage.

Nucleic acids isolated from biological samples treated with the disclosed preservative composition may be used in downstream analysis, including diagnostic applications and non-invasive prenatal testing (NIPT). As the disclosed preservative composition does not include aldehydes or other cross-linking agents, the risk of DNA damage and introduction of mutation artifacts may be avoided.

Preservative Composition

In one aspect, provided is a preservative composition for preserving nucleic acids—particularly, cell-free nucleic acids—in a biological sample, the composition comprising at least one volume excluding polymer, at least one osmotic agent and at least one enzyme inhibitor. Unexpectedly, it was found that this combination of components allows for cell-free nucleic acids in biological samples, such as cfDNA in plasma, to be preserved for at least 28 days at room temperature, which is more than twice as long as commercially available cell-free DNA preservatives, such as Streck Cell-Free DNA™ from Streck Inc. (Omaha, USA). Advantageously, the disclosed preservative composition does not rely on the use of aldehydes. It was further surprisingly found that samples treated with the disclosed preservative composition had minimal gDNA contamination resulting from cell lysis, even when the samples were subjected to movement and shaking (e.g., as would be experienced during shipping). Accordingly, the disclosed composition may also be used to preserve cells in a biological sample, such as white blood cells or circulating tumour cells.

Without being bound by theory, it is believed that the volume excluding polymer and the osmotic agent act to stabilize cells and reduce cell lysis, thereby preventing the release of cell contents, including gDNA and nucleases. It is believed that the volume excluding polymer acts as a crowding agent, which forces cells out of solution, thereby preventing the cells from lysing and releasing gDNA that may contaminate the low abundance cell-free nucleic acids and nucleases that will degrade the cell-free nucleic acids. The osmotic agent acts to create a hypertonic solution, which causes water to be removed from the cells that are present in the sample, causing the cells to shrink (or shrivel). In combination with the volume excluding polymer, it is believed that this reduces cell lysis and the subsequent release of gDNA and nucleases. Further, the presence of an enzyme inhibitor will inactive nucleases present in the sample, thereby preventing or reducing degradation of the cell-free nucleic acids.

As the disclosed preservative composition has been found to reduce cell lysis, the preservative composition may also be used to preserve whole cells in a bodily fluid, such as circulating tumor cells. These cells may be preserved for up to 28 days or more when combined with the disclosed preservative composition.

Optionally, the preservative composition may further comprise metabolic inhibitors to reduce cell metabolism and cellular respiration within the cell. By preventing cell metabolism, degradation of the cell-free nucleic acids and lysis of the cells in the sample are believed to be further reduced.

The preservative composition may comprise any volume excluding polymer, which acts as a crowding agent and forces cells out of solution. Examples of suitable volume excluding polymers include, but are not limited to, polyethylene glycol (PEG), glycerol, trehalose, dextrans and derivatives such as dextran sulfate and dextran acetate, and hydrophilic polymers such as polyvinyl alcohol, polyvinyl acetate and polyvinyl sulfate. Volume-excluding polymers having a molecular weight between 1000 and 1,000,000 daltons have been found to be particularly suitable for use in the preservative composition. In a preferred embodiment, the volume-excluding polymer is PEG. PEGs of differing molecular weights may be used, including but not limited to PEG 2000, PEG 4000, PEG 6000 and PEG 8000. More preferably, the volume excluding polymer is PEG 8000 (also referred to as PEG-8K).

The preservative composition preferably comprises about 10% to 50% w/w of the volume excluding polymer, preferably about 10% to 40% w/w of the volume excluding polymer, more preferably about 15% to 35% w/w of the volume excluding polymer and even more preferably about 20% to about 30% w/w of the volume excluding polymer.

The preservative composition may comprise any osmotic agent that creates a hypertonic solution and thereby causes water to be removed from the cells and causes the cells to shrink when a sufficient quantity of the preservative composition is added to a biological sample comprising cells. Examples of suitable osmotic agents include, but are not limited to, salts such as NaCl, KCl and $CaCl_2$), and sugars such as glucose or sucrose. In a preferred embodiment, the osmotic agent is NaCl.

The preservative composition preferably comprises about 1% to 20% w/w of the osmotic agent, more preferably about 1% to 15% w/w of the osmotic agent and even more preferably about 1% to about 10% w/w of the osmotic agent.

The preservative composition further comprises an enzyme inhibitor that works to inhibit nucleases. The enzyme inhibitors may include chelators to inhibit metal-dependent nucleases, and/or other components known to inhibit non-metal dependent nucleases. Examples of suitable enzyme inhibitors include, but are not limited to, ethylenediamine tetraacetic acid (EDTA), HEDTA, citrate, oxalate, aurintricarboxylic acid (ATA), DTT and any combination thereof. Preferably, the enzyme inhibitor is EDTA. Alternately, the enzyme inhibitor may be a citrate, such as sodium citrate or potassium citrate.

The preservative composition preferably comprises about 1% to about 30% of the enzyme inhibitor, more preferably about 1% to 20% w/w of the enzyme inhibitor and even more preferably about 1% to about 10% w/w of the enzyme inhibitor.

Optionally, the preservative composition may further comprise a metabolic inhibitor that acts to inhibit cellular processes such as cell metabolism and cellular respiration. Preferably, the metabolic inhibitor is sodium azide.

The preservative composition preferably comprises about 0.01% to about 10% of the metabolic inhibitor, more preferably about 0.01% to 5% w/w of the metabolic inhibitor and even more preferably about 0.01% to about 2% w/w of the metabolic inhibitor.

In a preferred embodiment, the preservative composition comprises:
  PEG as the volume excluding polymer, wherein the PEG is present in amount of about 10% to 50% w/w, preferably about 10% to 40%, more preferably about 15% to 35% w/w and even more preferably about 20% to about 30% w/w of the total composition;
  NaCl as the osmotic agent, wherein the NaCl is present in an amount of about 1% to 20% w/w, more preferably about 1% to 15% w/w and even more preferably about 1% to about 11% w/w of the total composition;
  EDTA as the enzyme inhibitor, wherein the EDTA is present in an amount of about 1% to about 30% w/w, more preferably about 1% to about 20% w/w, and even more preferably about 1% to about 10% w/w of the total composition; and
  sodium azide as the metabolic inhibitor, wherein the sodium azide is present in an amount of about 0.01% to about 10% w/w, more preferably about 0.01% to about 5% w/w, and even more preferably about 0.01% to about 2% w/w of the total composition;

The preservative composition can be prepared using a suitable solvent such as water or a buffered aqueous solution. Generally, the preservation composition is prepared by first dissolving the volume excluding polymer (e.g. such as PEG) in the suitable solvent (e.g. such as water), followed by the addition of the osmotic agent, the enzyme inhibitor and optionally, the metabolic inhibitor. The resulting solution may be adjusted to about a neutral pH. The preservative composition may be provided as an aqueous solution for use for the preservation of nucleic acids in a biological sample or for the preservation of cells (e.g. such as circulating tumour cells) in a biological sample. Alternatively, the aqueous composition may be lyophilized and the preservative composition may be provided in dry form for use or can be reconstituted with a suitable carrier prior to use.

While the preceding discussion contemplates the use of a pre-prepared preservative composition comprising the volume excluding polymer, the osmotic agent, the enzyme inhibitor and the optional metabolic inhibitor, which is added to the biological sample to be treated, it is also contemplated that the disclosed preservative composition may be constituted during use, by separately adding (in any order or simultaneously) the composition components to the biological sample to be treated. For example, blood collection tubes containing EDTA or sodium citrate (which are both suitable enzyme inhibitors of the disclosed preservative composition) are readily available. Accordingly, blood collected into such tubes would already contain the enzyme inhibitor component of the disclosed preservative composition. Appropriate amounts of the remaining components of the preservative components can then be added individually (in any order or simultaneously) to the blood sample, which already includes the enzyme inhibitor, to provide the desired final quantities of the volume excluding polymer, the osmotic agent, and the optional metabolic inhibitor (see discussion below, which describes preferred amounts of each component in the sample/preservative mixture). Alternatively, the volume excluding polymer, the osmotic agent, and the optional metabolic inhibitor can be mixed together beforehand and an appropriate amount of the mixture added to the blood sample (which already includes the enzyme inhibitor) to constitute the preservative composition.

Method for Preserving Nucleic Acids and/or Cells in a Biological Sample

In a further aspect, provided is a method for preserving nucleic acids in a biological sample, comprising the steps of: providing a preservative composition comprising at least one volume excluding polymer, at least one osmotic agent and at least one enzyme inhibitor and contacting the biological sample with the preservative composition to provide a treated sample.

The method can be carried out using the preservative composition as described in further detail above. The preservative composition may optionally further comprise a metabolic inhibitor.

The preservative composition can be provided as a liquid and more preferably, as an aqueous solution. The aqueous solution may be provided contained in a tube (such as an evacuated blood collection tube), syringe, an ampule, a dissolvable capsule, a permeable sack or other vehicle. The preservative composition can also be provided in solid form such as granules or tablets. The preservative composition can also be prepared as an aqueous solution, which is then lyophilized. The lyophilized preservative composition can then be provided in dry form for use or can be reconstituted with a suitable carrier prior to use.

The biological sample may be any biological fluid containing nucleic acids, including but not limited to blood, plasma, serum, urine, saliva, stool, breast milk, tears, sweat, cerebral spinal fluid, synovial fluid, semen, vaginal fluid, ascitic fluid, amniotic fluid, cell culture media and other biological fluids. The biological fluid may come from any source, including but not limited to prokaryotes, eukaryotes, bacteria, fungi, yeast, invertebrates, vertebrates, reptiles, fish, insects, plants or animals. In a preferred embodiment, the biological fluid is whole blood. The biological sample may include cells or may be free of cells. The nucleic acids preserved by the method disclosed herein can be cell-free RNA, cell-free DNA or any combination thereof. In a preferred embodiment, the nucleic acids are cell-free plasma DNA.

The biological sample can be collected directly or indirectly into any suitable container and a suitable amount of the preservative composition added to the biological sample to preserve the nucleic acids. In one embodiment, the biological sample is preferably a blood sample, and more preferably a human blood sample. In a preferred embodiment, a predetermined amount of the preservative composition is provided preloaded in a container or sample collection device, such as an evacuated tube, into which the blood sample can be directly collected, such that the blood sample immediately comes into contact with the preservative composition.

The ratio of preservative composition to biological sample may be from about 1:10 to 1:1, preferably about 1:5 and more preferably about 1:4. In a preferred embodiment, about 2 mL of the preservative composition can be added to about 8 mL of whole blood. In a further preferred embodiment, about 1.5 mL of the preservative composition can be added to about 8.5 mL of whole blood. It is contemplated that the amount of the preservative composition to be added to a biological sample for preservation of the nucleic acids contained in the biological sample can be determined by the person skilled in the art by routine experimentation.

In another embodiment, provided is a method for preserving nucleic acids in a biological sample comprising contacting the biological sample with, in any order or simultaneously, at least one volume excluding polymer, at least one osmotic agent and at least one enzyme inhibitor to provide a treated sample.

In such an embodiment, rather than employing a preservative composition preparation comprising the volume excluding polymer, the osmotic agent, the enzyme inhibitor and the optional metabolic inhibitor, the disclosed preservative composition is constituted by adding or contacting, in any order or simultaneously, the preservative composition components to the sample to be treated. For example, in embodiments wherein the biological sample is whole blood, the sample can be collected in to a standard blood collection tube comprising EDTA or a citrate as the enzyme inhibitor component of the preservative composition. Examples of such blood collection tubes include, but are not limited to, BD EDTA (K2) blood collection tubes (Cat #366643; Becton Dickinson, Mississauga, Canada) and BD Vacutainer® Sodium Citrate blood collection tubes (Cat #369714; Becton Dickinson, Mississauga, Canada). Following collection of the blood into the collection tube containing the enzyme inhibitor, the remaining components of the preservative composition (e.g. the volume excluding polymer, the osmotic agent, and optionally, the metabolic inhibitor) can be added to the blood sample individually in any order or preferably, as a pre-prepared composition. The pre-prepared composition can be provided as an aqueous solution or in solid form, such as granules or tablets. The pre-prepared composition can also be prepared as an aqueous solution, which is then lyophilized. The lyophilized composition can then be provided in dry form for use or can be reconstituted with a suitable carrier prior to use. Alternatively, the volume excluding polymer, the osmotic agent, and optionally, the metabolic inhibitor, can be added individually to the sample contained in the blood collection tube.

In a preferred embodiment, following contact of the biological sample with the at least one volume excluding polymer, the at least one osmotic agent, the at least one enzyme inhibitor, and optionally, the metabolic inhibitor, the amount of the at least one volume excluding polymer, preferably PEG, is about 2% to about 10% w/w of the treated sample, preferably about 2% to about 8% w/w of the treated sample; more preferably about 3% to 7% w/w of the treated sample, and even more preferably about 4% to 6% w/w of the treated sample;

the amount of the at least one osmotic agent, preferably NaCl, is about 0.2% to about 4% w/w of the treated sample, more preferably about 0.2% to 3% w/w of the treated sample, and even more preferably about 0.2% to 2% w/w of the treated sample;

the amount of the at least one enzyme inhibitor, preferably EDTA, is about 0.2% to about 6% w/w of the treated sample; more preferably about 0.2% to 4% w/w of the treated sample, and even more preferably about 0.2% to 2% w/w of the treated sample; and the amount of the optional metabolic inhibitor, preferably sodium azide, is about 0.002% to about 2% w/w of the treated sample, more preferably about 0.002% to 1% w/w of the treated sample, and even more preferably about 0.002% to 0.4% w/w of the treated sample.

Following contact of the biological sample with the preservative composition-either by the addition of a preparation of the preservative composition to the biological sample or by addition of the individual components of the preservative composition to the biological sample—the resulting sample/preservative mixture (also referred to herein as the "treated sample") may be stored for a period of time prior to further processing (e.g. separation of plasma from whole blood samples) and the isolation of the nucleic acids contained in the sample. The treated sample may be stored, either under refrigeration or at ambient temperatures, for a period of least 1 day, at least 7 days, at least 14 days, at least 21 days, at least 28 days, or at least 40 days. At least a portion of the storage period may occur at ambient temperature.

As used herein, the preservation time for a cell-free nucleic acid is the length of time from the initial contact of the preservative composition with a biological sample containing the cell-free nucleic acid to the isolation of the cell-free nucleic acid. In a preferred embodiment, the biological sample may be a blood sample and contact with the preservative composition may be within 1 minute from blood draw. In preferred embodiments, the cell-free nucleic acids, and more preferably cell-free plasma DNA, can be isolated from the blood sample at least 1 day, at least 7 days, at least 14 days, at least 21 days, at least 28 days, and at least 40 days after contacting the blood sample with the preservative composition. In such embodiments, the preservation time for the cell-free plasma DNA preserved using the disclosed preservative composition and method, may be anywhere between 1 minute and over 28 days.

The preserved cell-free nucleic acids can be isolated from the treated biological sample using any method known in the art. Suitable methods include, but are not limited to the use of phenol/chloroform, the use of silicon carbide, and the use of silica. In a preferred embodiment, the purified nucleic acids may be used for downstream analysis. The downstream analysis may be any method known in the art, including PCR, microarrays and sequencing applications, including next generation sequencing. The downstream analysis may be for the purpose of diagnostic applications, including but not limited to, diagnostic applications associated with cancer diagnosis and monitoring, the monitoring and diagnosis of viral infections, and for non-invasive prenatal testing (NIPT).

In a further aspect, provided is a method for preserving cells in a biological sample comprising the steps of: providing a preservative composition comprising at least one volume excluding polymer, at least one osmotic agent and at least one enzyme inhibitor; and contacting the biological sample with the preservative composition to provide a treated sample.

The method can be carried out using the preservative composition as described in further detail above. The biological sample containing cells to be preserved can be any of the biological fluids described above and can be collected as described above. In a preferred embodiment, the cells to be preserved are circulating tumour cells from a blood sample. The ratio of preservative composition to biological sample may be from about 1:10 to 1:1, preferably about 1:5 and more preferably about 1:4. In a preferred embodiment, about 2 mL of the preservative composition can be added to about 8 mL of whole blood. In another preferred embodiment, about 1.5 mL of the preservative composition can be added to about 8 mL of whole blood. The amount of the preservative composition to be added to a biological sample for preservation of the cells contained in the biological sample can be determined by the person skilled in the art by routine experimentation. The resulting treated samples can be stored for an extended period as described in further detail above.

In another aspect, provided is a method for preserving cells in a biological sample comprising contacting the biological sample with, in any order or simultaneously, at least one volume excluding polymer, at least one osmotic agent and at least one enzyme inhibitor to provide a treated sample.

In an embodiment, the biological sample is first contacted with the at least one enzyme inhibitor by collecting the biological sample into a container containing the enzyme inhibitor. The at least one volume excluding polymer and the at least one osmotic agent are then added to the container containing the biological sample and the at least one enzyme inhibitor to provide the treated sample. In a preferred embodiment, the biological sample containing cells to be preserved is whole blood and the container containing the at least one enzyme inhibitor is a standard blood collection tube containing EDTA or a citrate, such as described in further detail above. In a further preferred embodiment, the cells to be preserved are circulating tumour cells from a blood sample. Preferably, following contact of the biological sample with the at least one volume excluding polymer, the at least one osmotic agent, the at least one enzyme inhibitor, and optionally, the metabolic inhibitor:

the amount of the at least one volume excluding polymer, preferably PEG, is about 2% to about 10% w/w of the treated sample, preferably about 2% to about 8% w/w of the treated sample; more preferably about 3% to 7% w/w of the treated sample, and even more preferably about 4% to 6% w/w of the treated sample;

the amount of the at least one osmotic agent, preferably NaCl, is about 0.2% to about 4% w/w of the treated sample, more preferably about 0.2% to 3% w/w of the treated sample, and even more preferably about 0.2% to 2% w/w of the treated sample;

the amount of the at least one enzyme inhibitor, preferably EDTA, is about 0.2% to about 6% w/w of the treated sample; more preferably about 0.2% to 4% w/w of the treated sample, and even more preferably about 0.2% to 2% w/w of the treated sample; and the amount of the optional metabolic inhibitor, preferably sodium azide, is about 0.002% to about 2% w/w of the treated sample, more preferably about 0.002% to 1% w/w of the treated sample, and even more preferably about 0.002% to 0.4% w/w of the treated sample.

The resulting treated samples can be stored for an extended period as described in further detail above.

Kit for Preserving Nucleic Acids and/or Cells in a Biological Sample

In a further aspect, provided are kits that can be used for the preservation of nucleic acids, and in particular, cell-free nucleic acids, in a biological sample. In another embodiment, the kit may be used for the preservation of cells, and in particular, circulating tumour cells, in a biological sample. The kits may be used to carry out the methods described above.

In one embodiment, the kit comprises a preservative composition comprising at least one volume excluding polymer, at least one osmotic agent, at least one enzyme inhibitor and instructions on how to combine the biological sample with the preservative composition to provide a treated sample. The preservation composition may be provided in a package having the instructions printed on the package or in a package along with an instructional insert.

The kit may comprise the preservative composition as described in further detail above. The preservative composition may optionally further comprise a metabolic inhibitor.

In a preferred embodiment, the kit can further comprise a blood collection tube, containing a predetermined volume of the preservative composition and instructions on how to collect a blood sample into the tube, including the amount of blood to be collected. In one embodiment, the tube will contain about 2 ml of the preservation composition and the instructions will instruct the user to collect about 8 ml blood sample into the tube. In another embodiment, the tube will contain about 1.5 ml of the preservation composition and the instructions will instruct the user to collect about 8.5 ml blood sample into the tube. The blood collection tube containing the predetermined volume of the preservative composition may be provided in a package having the instructions printed on the package or in a package along with an instructional insert.

In another embodiment, provided is a kit comprising:
at least one volume excluding polymer,
at least one osmotic agent,
optionally, a metabolic inhibitor; and
instructions to combine the at least one volume excluding polymer, the at least one osmotic agent and optionally, the metabolic inhibitor with a biological sample and at least one enzyme inhibitor, in any order or simultaneously, to provide a treated sample;
wherein the amount of the at least one volume excluding polymer, preferably PEG, is about 2% to about 10% w/w of the treated sample, preferably about 2% to about 8% w/w of the treated sample; more preferably about 3% to 7% w/w of the treated sample, and even more preferably about 4% to 6% w/w of the treated sample;

wherein the amount of the at least one osmotic agent, preferably NaCl, is about 0.2% to about 4% w/w of the treated sample, more preferably about 0.2% to 3% w/w of the treated sample, and even more preferably about 0.2% to 2% w/w of the treated sample;

wherein the amount of the at least one enzyme inhibitor, preferably EDTA, is about 0.2% to about 6% w/w of the treated sample; more preferably about 0.2% to 4% w/w of the treated sample, and even more preferably about 0.2% to 2% w/w of the treated sample; and wherein the amount of the optional metabolic inhibitor, preferably sodium azide, is about 0.002% to about 2% w/w of the treated sample, more preferably about 0.002% to 1% w/w of the treated sample, and even more preferably about 0.002% to 0.4% w/w of the treated sample.

The at least one volume excluding polymer, the at one osmotic agent, and the optional metabolic inhibitor can be provided separately (e.g. in separate containers), along with instructions to combine the individual components with the biological sample and the at least one enzyme inhibitor to provide a treated sample, wherein the relative amounts of the volume excluding polymer, the osmotic agent, the enzyme inhibitor, and the optional metabolic inhibitor are as described in the previous paragraph. Alternatively, the at least one volume excluding polymer, the at least one osmotic agent, and the optional metabolic inhibitor can be provided as a pre-prepared composition along with instructions to combine the composition with the biological sample and the at least one enzyme inhibitor to provide the treated sample. The components of the kit may be provided in a package having the instructions printed on the package or in a package along with an instructional insert.

Use of the kit results in the disclosed preservative composition being constituted upon mixing the composition comprising the at least one volume excluding polymer and the at least one osmotic agent together with the at least one enzyme inhibitor. The composition comprising the at least one volume excluding polymer and the at least one osmotic agent—and optionally, a metabolic inhibitor and wherein the amount of metabolic inhibitor is about 0.001% to about 0.01% w/w of the of the total weight of the treated sample, more preferably about 0.002% to 0.01% w/w of the treated sample, and even more preferably about 0.005% to 0.01% w/w of the treated sample—can be provided as an aqueous form or in dry form as described in further detail above. In an embodiment, a suitable amount of the at least one enzyme inhibitor can be provided in a container in which the biological sample is to be collected. In a preferred embodiment, the biological sample is whole blood and the container is a standard blood collection container containing EDTA and/or a citrate, examples of which, are described above.

An advantage of the disclosed kits, and in particular, kits comprising blood collection tubes containing the disclosed preservative composition (or alternatively, kits comprising a composition comprising at least one volume excluding polymer and at least one osmotic agent to be added to a blood collection tube containing the enzyme inhibitor to constitute the disclosed preservative composition), may be the reduction of gDNA contamination of the plasma cell-free nucleic acids resulting from cell lysis during storage and transport. Blood samples are often collected in one location and then shipped to a centralized lab or core facility for plasma preparation and isolation of cell-free nucleic acids from the plasma samples for downstream analysis and diagnostic applications. Movement during shipping may lead to lysis of cells, which in turn can cause an increase in the release of gDNA into the plasma fraction. With the disclosed kits, it is believed that the combination of the volume excluding polymer and the osmotic agent comprising the preservative composition causes cells present in the blood samples to clump together, thereby decreasing cell lysis during transport and storage. Blood samples collected into tubes containing the disclosed preservative form sediment in the bottom of the tube, which does not easily go back into suspension when inverted by hand. Such sedimentation is not observed in blood samples collected in conventional EDTA tubes or tubes comprising aldehyde preservatives (such as Streck Cell-Free DNA™ BCT, Streck Inc., Omaha, USA).

As use of the disclosed preservative composition helps to minimize cell lysis in the biological sample, the disclosed kit, and in particular, a kit comprising blood collection tubes containing the disclosed preservative composition (or alternatively, kits comprising a composition comprising at least one volume excluding polymer, at least one osmotic agent and optionally, a metabolic inhibitor, to be added to a blood collection tube containing the enzyme inhibitor to constitute the disclosed preservative composition), may also be used to preserve cells in a bodily fluid. In one preferred embodiment, the disclosed kit may be used to preserve circulating tumor cells within bodily fluids. These cells may be preserved for up to 28 days or more when combined with the disclosed preservative composition.

Use of the disclosed kit can enable whole blood samples to be collected, stored and shipped at ambient conditions, extending the timeframe for plasma processing to over 28 days. Accordingly, the disclosed kit may be of particular benefit for remote locations and resource-limited settings, where additional time may be required between blood collection and plasma processing. The disclosed kit may allow for easier shipping and storage for longer periods of time than conventional preservatives (such as aldehyde based preservatives), thereby facilitating centralized processing and analysis and increasing the availability of cfDNA testing for diagnostic applications for the broad population.

Further, in contrast to the use of commercially available tubes, such as Streck Cell-Free DNA™ BCT (Streck Inc., Omaha, USA), the blood collection tubes of the disclosed kit contain a preservative composition that is free of aldehydes. Therefore, the problems associated with aldehydes, including DNA damage, can be avoided with the disclosed kit. While the prior art tubes include a quenching agent to help protect against the deleterious effects of free aldehydes on DNA, the risks associated with aldehyde use cannot be entirely eliminated as the prior art preservatives rely on aldehyde fixation for cell stabilization.

While only specific embodiments of the invention have been described, it is apparent that variations can be made thereto without departing from the scope of the invention. The invention is further illustrated by the following examples, which are not to be construed in any way as imposing limitations upon the scope thereof. It is the intention in the appended claims to cover all variations that may fall within the true scope of the invention.

EXAMPLES

These examples are described for the purposes of illustration and are not intended to limit the scope of the invention.

Example 1—Improved Preservation of Cell-Free Plasma DNA Over Extended Storage Periods at Ambient Temperature Two variations of the preservative composition disclosed herein were prepared. Nucleic Acid Preservative A comprised 33% w/w PEG; 5% w/w NaCl; 2% w/w EDTA; 0.023% w/w sodium azide and the balance, water. Nucleic Acid Preservative B comprised 25% w/w PEG; 3% w/w NaCl; 3% w/w EDTA; 0.033% w/w sodium azide and the balance, water.

Blood samples from a single healthy donor were drawn into 9 separate blood collection tubes (Tubes 1 to 9).

Tube 1 was a BD plain blood collection tube (BD Vacutainer® Serum Cat #366430; Becton Dickinson, Mississauga, Canada) containing between 8 and 10 ml of blood and approximately 2 mL of Nucleic Acid Preservative A.

Tube 2 was a BD citrate blood collection tube (BD Vacutainer® Sodium Citrate Tube Cat #369714; Becton Dickinson, Mississauga, Canada) containing between 4 and 5 mL of blood and approximately 1 mL of Nucleic Acid Preservative A.

Tube 3 was a BD EDTA blood collection tube (BD EDTA (K2) Tube Cat #366643; Becton Dickinson, Mississauga, Canada) containing between 8 and 10 mL of blood and approximately 2 mL of Nucleic Acid Preservative A.

Tube 4 was a BD plain blood collection tube (BD Vacutainer® Serum Cat #366430; Becton Dickinson, Mississauga, Canada) containing between 8 and 10 ml of blood and approximately 2 mL of Nucleic Acid Preservative B.

Tube 5 was a BD citrate blood collection tube (BD Vacutainer® Sodium Citrate Tube Cat #369714; Becton Dickinson, Mississauga, Canada) containing between 4 and 5 mL of blood and approximately 1 mL of Nucleic Acid Preservative B.

Tube 6 was a BD EDTA blood collection tube (BD EDTA (K2) Tube Cat #366643; Becton Dickinson, Mississauga, Canada) containing between 8 and 10 mL of blood and approximately 2 mL of Nucleic Acid Preservative B.

Tube 7 was a BD citrate blood collection tube (BD Vacutainer® Sodium Citrate Tube Cat #369714; Becton Dickinson, Mississauga, Canada) containing between 4 and 5 mL of blood.

Tube 8 was a BD EDTA blood collection tube (BD EDTA (K2) Tube Cat #366643; Becton Dickinson, Mississauga, Canada) containing between 8 and 10 mL of blood.

Tube 9 was a Streck Cell-Free DNA™ BCT tube (Catalog #218962; Streck, Omaha, USA) containing between 8 and 10 mL of blood.

All tubes were mixed by inversion and then aliquots of 1 mL were dispensed into Eppendorf tubes and stored at room temperature. Aliquots of treated blood were processed at each time point starting with day 0 (processed immediately), day 7, day 14, day 21 and then day 28. The plasma was separated by centrifugation for 15 minutes at 400× g (2,000 RPM) followed by transferring the plasma into a new tube. DNA was then isolated from the plasma samples using Norgen's Plasma/Serum Cell-Free Circulating DNA Purification Micro Kit (Cat #55500, Norgen Biotek, Thorold, Canada) according to the manufacturer's instructions.

The purified cell-free plasma DNA was then analyzed using Real-Time PCR amplification of the Alu247 (fragments of 247 bp) and Alu115 (fragments of 115 bp) gene targets. The highly abundant ALU sequences can be used to quantify human genomic DNA based on size. cfDNA typically exhibits a narrow size range distribution around 165 bp. Therefore, Alu115 can be used to detect total cfDNA and high molecular weight gDNA, while Alu247 can be used to detect the presence of high molecular weight cellular gDNA contamination (Swift Biosciences Technical Note, 2016). An increase in the larger Alu247 fragment is indicative of cell lysis, and therefore, is indicative of the sample no longer being preserved.

The conditions of the real-time PCR were:

Real Time PCR Mix:
 3 μL of Plasma DNA
 10 μL Norgen's 2× PCR Master Mix (Cat #28007, Norgen Biotek, Thorold, Canada)
 0.12 μL Alu247 or Alu115 Forward Primer (50 μM)
 0.12 μL Alu247 or Alu115 Reverse Primer (50 μM)
 0.03 μL 100× Syber Green Mix (Catalog #170-8880, BioRad, Hercules, USA)
 6.73 μL Water
 20 μL PCR Reaction Real-Time PCR Program:
 Cycle 1: (1×)
  Step 1: 95.0° C. for 03:00
 Cycle 2: (45×)
  Step 1: 95.0° C. for 00:30
  Step 2: 64.0° C. for 00:30
  Step 3: 72.0° C. for 00:30
  Data collection and real-time analysis enabled.
 Cycle 3: (1×)
  Step 1: 57.0° C. for 01:00
 Cycle 4: (80×)
  Step 1: 57.0° C. for 00:10
  Increase setpoint temperature after cycle 2 by 0.5° C.
  Melt curve data collection and analysis enabled.

Figure 2:
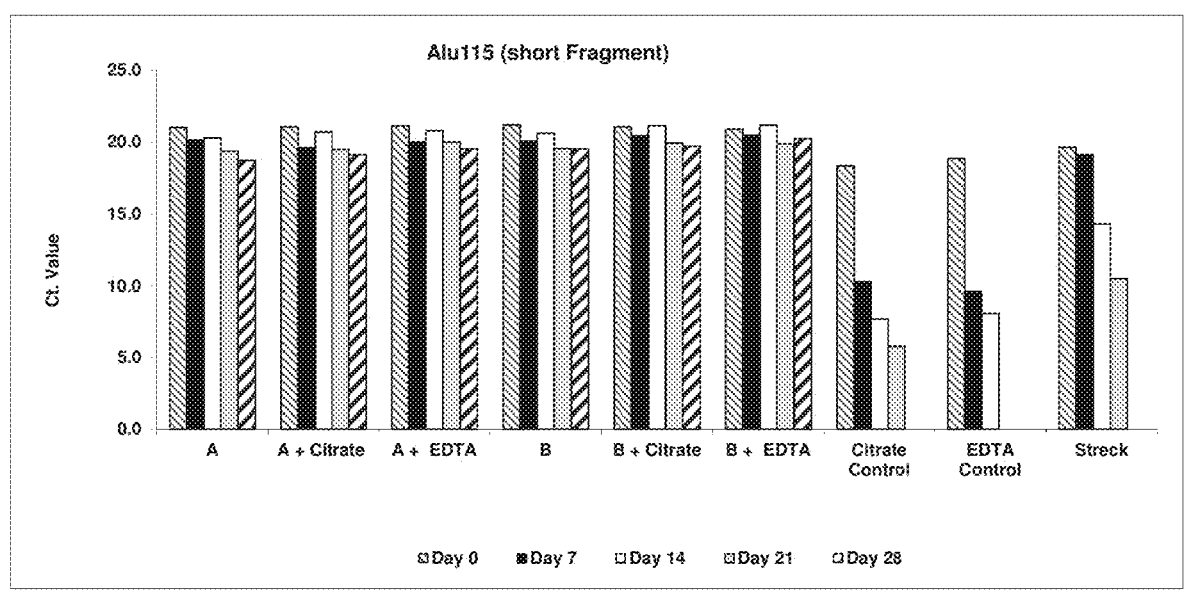
FIG. 2 is a graph showing the preservation of cfDNA in blood samples, stored for a period of up to 28 days, by detecting Alu115 fragments using real time PCR. DNA was isolated from blood collected into: preservative tubes comprising preservative compositions as disclosed herein (A; A+Citrate; A+EDTA; B, B+Citrate; B+EDTA); a preservative tube containing a prior art preservative composition (Streck), a preservative tube containing citrate (Citrate Control) or a preservative tube containing EDTA (EDTA Control).

The Ct (cycle threshold) values generated from each time point and from the 9 different tubes were then summarized in Table 1 for the Alu247 amplification and Table 2 for the Alu115 amplification. The Ct values were also plotted as shown in FIG. 1 and FIG. 2.

TABLE 1

Alu247 (long fragment) Ct

| Tube | Preservative | Day 0 | Day 7 | Day 14 | Day 21 | Day 28 |
|---|---|---|---|---|---|---|
| 1 | A | 20.9 | 21.2 | 20.5 | 19.6 | 20.0 |
| 2 | A + Citrate | 21.6 | 19.4 | 21.5 | 20.2 | 21.2 |
| 3 | A + EDTA | 21.2 | 21.2 | 22.0 | 20.5 | 21.5 |
| 4 | B | 21.5 | 21.5 | 21.5 | 19.6 | 21.0 |
| 5 | B + Citrate | 21.0 | 22.2 | 22.5 | 20.4 | 21.5 |
| 6 | B + EDTA | 21.5 | 21.9 | 22.9 | 21.4 | 22.5 |
| 7 | Citrate Control | 16.5 | 7.6 | 4.8 | 3.2 | N/A |
| 8 | EDTA Control | 17.7 | 7.7 | 5.2 | N/A | N/A |
| 9 | Streck Cell-Free DNA ™ BCT | 19.6 | 18.8 | 12.8 | 8.3 | N/A |

TABLE 2

Alu115 (short fragment) Ct

| Tube | Preservative | Day 0 | Day 7 | Day 14 | Day 21 | Day 28 |
|---|---|---|---|---|---|---|
| 1 | A | 21.0 | 20.1 | 20.3 | 19.4 | 18.7 |
| 2 | A + Citrate | 21.1 | 19.6 | 20.7 | 19.5 | 19.1 |

TABLE 2-continued

Alu115 (short fragment) Ct

| Tube | Preservative | Day 0 | Day 7 | Day 14 | Day 21 | Day 28 |
|---|---|---|---|---|---|---|
| 3 | A + EDTA | 21.1 | 20.0 | 20.8 | 20.0 | 19.5 |
| 4 | B | 21.2 | 20.1 | 20.6 | 19.6 | 19.5 |
| 5 | B + Citrate | 21.1 | 20.5 | 21.1 | 19.9 | 19.7 |
| 6 | B + EDTA | 20.9 | 20.5 | 21.2 | 19.9 | 20.2 |
| 7 | Citrate Control | 18.3 | 10.3 | 7.7 | 5.8 | N/A |
| 8 | EDTA Control | 18.9 | 9.6 | 8.1 | N/A | N/A |
| 9 | Streck Cell-Free DNA ™ BCT | 19.6 | 19.1 | 14.3 | 10.5 | N/A |

As discussed above, if cell lysis occurs, then the longer Alu247 fragments would increase and the Ct values would decrease. As shown in Table 1 and FIG. 1, Nucleic Acid Preservative A (alone or in combination with citrate or EDTA) and Nucleic Acid Preservative B (alone or in combination with citrate or EDTA) preserved the samples for up to 28 days, as evidenced by the consistent Ct readings from day 0, day 7, day 14, day 21 and day 28. In contrast, EDTA alone and citrate alone resulted in cell lysis by day 7, at which time the Ct values were observed to drop significantly. Nucleic Acid Preservative A and Nucleic Acid Preservative B were also shown to preserve the samples for a longer period as compared to the prior art Streck tubes, which showed lysis after 14 days. The observed preservation time for the Streck tubes corresponded to the preservation claims made by this product (i.e. up to 14 days). The improved preservation performance of the disclosed preservation compositions is also evident when looking at the smaller Alu115 fragment. As shown in Table 2 and FIG. 2, again Nucleic Acid Preservative A and Nucleic Acid Preservative B (alone or in combination with citrate or EDTA) allowed for preservation up to 28 days, while EDTA alone, citrate alone and the prior art Streck tubes show lysis by 14 days as indicated by the lower Ct value, corresponding to an increase in the amount of DNA present.

Example 2—Improved Preservation of Cell-Free Plasma DNA from Different Donors Over Extended Storage Periods at Ambient Temperature Blood samples from two healthy donors (Male-A and Female-B) were drawn into 4 separate blood collection tubes (Tubes 1 to 4) to show the reproducibility of the nucleic acid preservation when samples were tested from different donors.

Tube 1 was a BD plain blood collection tube (BD Vacutainer® Serum Cat #366430; Becton Dickinson, Mississauga, Canada) containing between 8 and 10 ml of blood and approximately 2 mL of Nucleic Acid Preservative A (see Example 1).

Tube 2 was a BD plain blood collection tube (BD Vacutainer® Serum Cat #366430; Becton Dickinson, Mississauga, Canada) containing between 8 and 10 ml of blood and approximately 2 mL of Nucleic Acid Preservative B (see Example 1).

Tube 3 was a BD EDTA blood collection tube (BD EDTA (K2) Tube Cat #366643; Becton Dickinson, Mississauga, Canada) containing between 8 and 10 mL of blood.

Tube 4 was a Streck Cell-Free DNA™ BCT tube (Catalog #218962; Streck, Omaha, USA) containing between 8 and 10 mL of blood.

All tubes were mixed by inversion and then aliquots of 1 mL were dispensed into Eppendorf tubes and stored at room temperature. Aliquots of treated blood were processed at each time point starting at day 0 (processed immediately), day 1, day 4, day 7, day 14, day 21 and then day 28. The plasma was separated by centrifugation for 15 minutes at 400× g (2,000 RPM) followed by transferring the plasma into a new tube. DNA was then isolated from the plasma samples using Norgen's Plasma/Serum Cell-Free Circulating DNA Purification Micro Kit (Cat #55500, Norgen Biotek, Thorold, Canada) according to the manufacturer's instructions.

The purified cell-free plasma DNA was then analyzed using Real-Time PCR amplification of the Alu247 and Alu115 gene targets.

The conditions of the real-time PCR were:
Real Time PCR Mix:
  3 µL of Plasma DNA
  10 µL Norgen's 2×PCR Master Mix (Cat #28007, Norgen Biotek, Thorold, Canada)
  0.12 µL Alu247 or Alu115 Forward Primer (50 µM)
  0.12 µL Alu247 or Alu115 Reverse Primer (50 µM)
  0.03 µL 100× Syber Green Mix (Catalog #170-8880, BioRad, Hercules, USA)
  6.73 µL Water
  20 µL PCR Reaction
Real-Time PCR Program:
Cycle 1: (1×)
  Step 1: 95.0° C. for 03:00
Cycle 2: (45×)
  Step 1: 95.0° C. for 00:30
  Step 2: 64.0° C. for 00:30
  Step 3: 72.0° C. for 00:30
  Data collection and real-time analysis enabled.
Cycle 3: (1×)
  Step 1: 57.0° C. for 01:00
Cycle 4: (80×)
  Step 1: 57.0° C. for 00:10
  Increase setpoint temperature after cycle 2 by 0.5° C.
  Melt curve data collection and analysis enabled.

Figure 3:
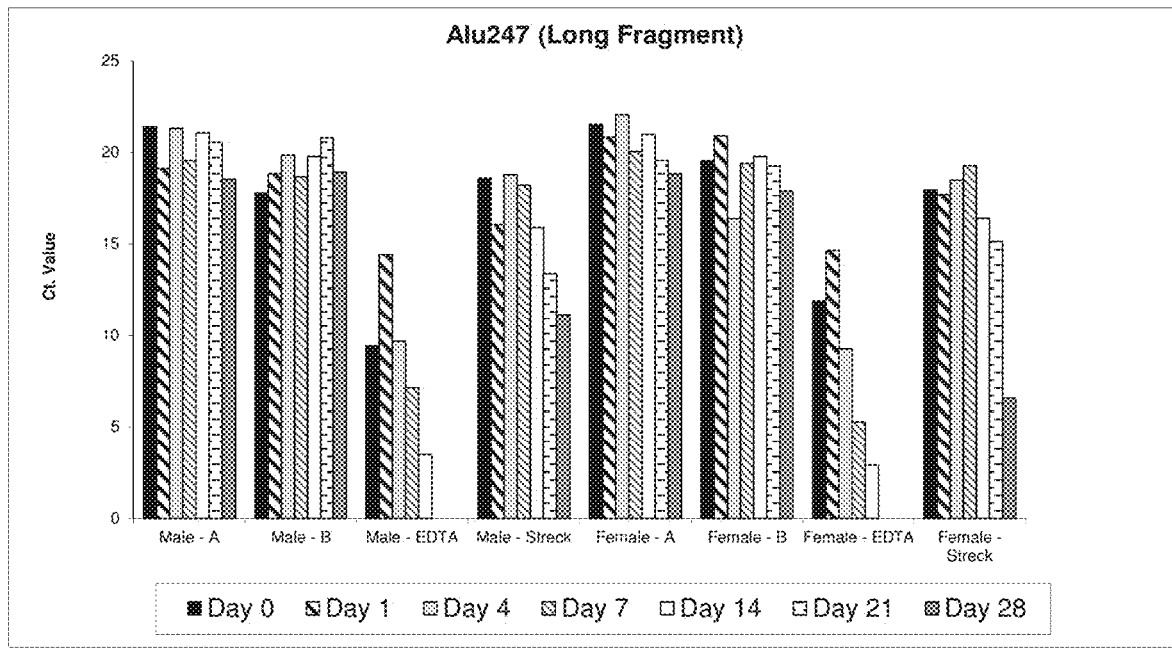
FIG. 3 is a graph showing gDNA contamination in blood samples, stored for a period of up to 28 days, by detecting Alu247 fragments using real time PCR. DNA was isolated from blood drawn from 2 different individuals (Male; Female) and collected into: preservative tubes containing preservative compositions as disclosed herein (A; B); a preservative tube containing a prior art preservative composition (Streck) or a preservative tube containing EDTA (EDTA).
Figure 4:
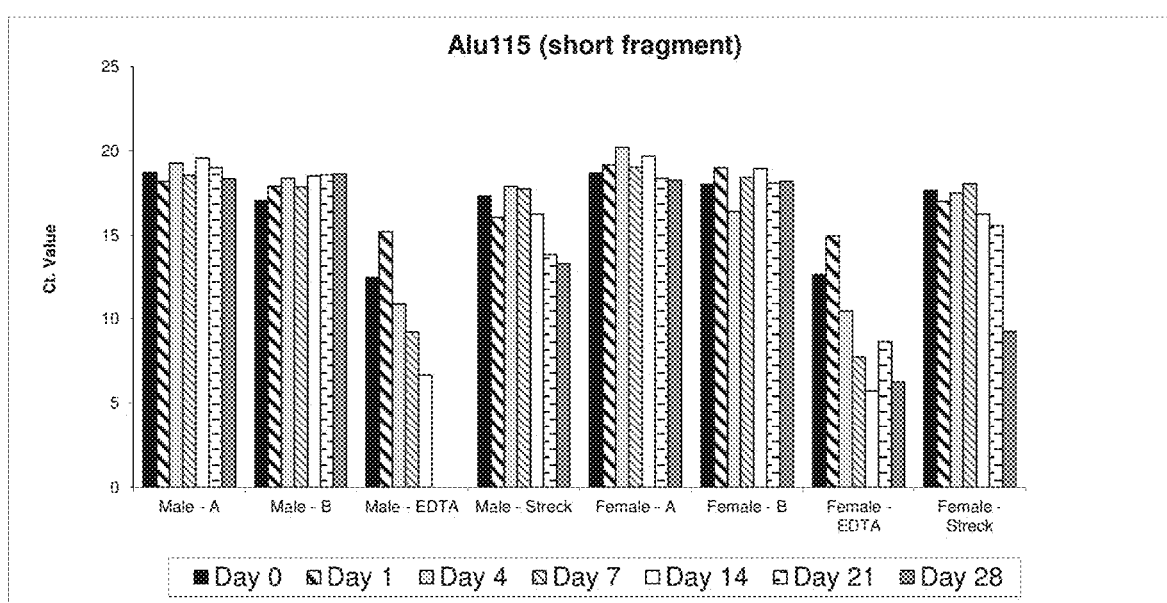
FIG. 4 is a graph showing the preservation of cfDNA in blood samples, stored for a period of up to 28 days, by detecting Alu115 fragments using real time PCR. DNA was isolated from blood drawn from 2 different individuals (Male; Female) and collected into: preservative tubes containing preservative compositions as disclosed herein (A; B); a preservative tube containing a prior art preservative composition (Streck) or a preservative tube containing EDTA (EDTA).

The Ct (cycle threshold) values generated from each time point for the 2 different individuals were then summarized. Table 3 shows the Ct values for the Alu247 amplification from the 2 different individuals, and Table 4 shows the Ct values for the Alu115 amplification from the 2 different individuals. The Ct values were also plotted as shown in FIG. 3 and FIG. 4.

TABLE 3

Alu247 Ct

| | Preservative | Day 0 | Day 1 | Day 4 | Day 7 | Day 14 | Day 21 | Day 28 |
|---|---|---|---|---|---|---|---|---|
| Male | A | 21.43 | 19.14 | 21.33 | 19.57 | 21.09 | 20.57 | 18.55 |
| | B | 17.79 | 18.85 | 19.86 | 18.68 | 19.79 | 20.81 | 18.94 |
| | EDTA | 9.44 | 14.43 | 9.69 | 7.15 | 3.50 | N/A | N/A |
| | Streck | 18.61 | 16.07 | 18.79 | 18.23 | 15.90 | 13.38 | 11.14 |

TABLE 3-continued

Alu247 Ct

|  | Preservative | Day 0 | Day 1 | Day 4 | Day 7 | Day 14 | Day 21 | Day 28 |
|---|---|---|---|---|---|---|---|---|
| Female | A | 21.54 | 20.84 | 22.09 | 20.06 | 20.99 | 19.57 | 18.85 |
|  | B | 19.56 | 20.92 | 16.39 | 19.41 | 19.79 | 19.27 | 17.90 |
|  | EDTA | 11.88 | 14.65 | 9.27 | 5.27 | 2.92 | N/A | N/A |
|  | Streck | 17.96 | 17.71 | 18.49 | 19.30 | 16.41 | 15.15 | 6.58 |

TABLE 4

Alu115 Ct

|  | Preservative | Day 0 | Day 1 | Day 4 | Day 7 | Day 14 | Day 21 | Day 28 |
|---|---|---|---|---|---|---|---|---|
| Male | A | 18.73 | 18.19 | 19.27 | 18.57 | 19.57 | 19.00 | 18.35 |
|  | B | 17.05 | 17.90 | 18.39 | 17.86 | 18.52 | 18.59 | 18.62 |
|  | EDTA | 12.49 | 15.20 | 10.88 | 9.23 | 6.66 | N/A | N/A |
|  | Streck | 17.31 | 16.05 | 17.89 | 17.75 | 16.24 | 13.86 | 13.31 |
| Female | A | 18.68 | 19.16 | 20.21 | 19.05 | 19.69 | 18.38 | 18.26 |
|  | B | 18.01 | 19.00 | 16.40 | 18.43 | 18.95 | 18.10 | 18.20 |
|  | EDTA | 12.66 | 14.96 | 10.46 | 7.73 | 5.71 | 8.64 | 6.24 |
|  | Streck | 17.66 | 17.00 | 17.50 | 18.05 | 16.25 | 15.57 | 9.25 |

As discussed above, if cell lysis occurs then the longer Alu247 fragment would increase and the Ct values would decrease. As shown in Table 3 and FIG. 3, Nucleic Acid Preservative A and Nucleic Acid Preservative B preserved the samples from both the male and female donor for up to 28 days, as evidenced by the consistent Ct readings from day 0, day 1, day 4, day 7, day 14, day 21 and day 28. In contrast, the EDTA tubes resulted in cell lysis immediately, as the Ct values are low. Also, it can be seen that Nucleic Acid Preservative A and Nucleic Acid Preservative B provided greater long term preservation (e.g. no substantial lysis observed at 28 days) as compared to the prior art Streck tubes, which showed lysis after only 14 days. The improved preservation performance of the disclosed preservation compositions is also evident when looking at the smaller Alu115 fragment. As shown in Table 4 and FIG. 4, again Nucleic Acid Preservative A and Nucleic Acid Preservative B allow for preservation up to 28 days for the blood samples from both the female and the male, while the EDTA tubes showed lysis almost immediately and prior art Streck tubes show lysis by 14 days.

Example 3—Improved Preservation of Cell-Free Plasma DNA Over Extended Storage Periods at Ambient Temperature and without the Use of Metabolic Inhibitors Two further variations of the preservative composition disclosed herein were prepared. Nucleic Acid Preservative C comprised 10% w/w PEG and 4.2% w/w NaCl, and the balance, water. Nucleic Acid Preservative D comprised 40% w/w PEG and 20% w/w NaCl, and the balance, water. The enzyme inhibitor (i.e. EDTA) component of the nucleic acid preservative composition was provided separately in the blood collection tube.

Blood samples from a single healthy donor were drawn into 3 separate blood collection tubes (Tubes 1 to 3).

Tube 1 was a BD EDTA blood collection tube (BD EDTA (K2) Tube Cat #366643; Becton Dickinson, Mississauga, Canada) containing between 8 and 10 ml of blood and approximately 2 mL of Nucleic Acid Preservative C.

Tube 2 was a BD EDTA blood collection tube (BD EDTA (K2) Tube Cat #366643; Becton Dickinson, Mississauga, Canada) containing between 8 and 10 ml of blood and approximately 1 mL of Nucleic Acid Preservative D.

Tube 3 was a Streck Cell-Free DNA™ BCT tube (Catalog #218962; Streck, Omaha, USA) containing between 8 and 10 mL of blood.

All tubes were mixed by inversion and then aliquots of 1 mL were dispensed into Eppendorf tubes and stored at room temperature. Aliquots of preserved blood were processed at each time point starting at day 1, day 7, day 13, day 22 and day 30. The plasma was separated by centrifugation for 15 minutes at 400× g (2,000 RPM) followed by transferring the plasma into a new tube. DNA was then isolated from the plasma samples using Norgen's Plasma/Serum Cell-Free Circulating DNA Purification Micro Kit (Cat #55500, Norgen Biotek, Thorold, Canada) according to the manufacturer's instructions.

The purified cell-free plasma DNA was then analyzed using Real-Time PCR amplification of the human 5S rRNA gene. Amplification of the 5S rRNA gene with a consistent Ct value would indicate that the DNA is being preserved within the sample and that no cell lysis is occurring. Once excessive cell lysis occurs, the plasma cannot be separated and collected from the samples. Therefore, plasma DNA cannot be isolated and no Ct values will be recorded (marked as N/A).

The conditions of the real-time PCR were:

Real Time PCR Mix:

3 μL of Plasma DNA

10 μL Norgen's 2×PCR Master Mix (Cat #28007, Norgen Biotek, Thorold, Canada)

0.12 μL Alu247 or Alu115 Forward Primer (50 μM)

0.12 μL Alu247 or Alu115 Reverse Primer (50 μM)

0.03 μL 100× Syber Green Mix (Catalog #170-8880, BioRad, Hercules, USA)

6.73 μL Water

20 μL PCR Reaction

Real-Time PCR Program:
  Cycle 1: (1×)
    Step 1: 95.0° C. for 03:00
  Cycle 2: (45×)
    Step 1: 95.0° C. for 00:30
    Step 2: 64.0° C. for 00:30
    Step 3: 72.0° C. for 00:30
    Data collection and real-time analysis enabled.
  Cycle 3: (1×)
    Step 1: 57.0° C. for 01:00
  Cycle 4: (80×)
    Step 1: 57.0° C. for 00:10
    Increase setpoint temperature after cycle 2 by 0.5° C.
    Melt curve data collection and analysis enabled.

Figure 5:
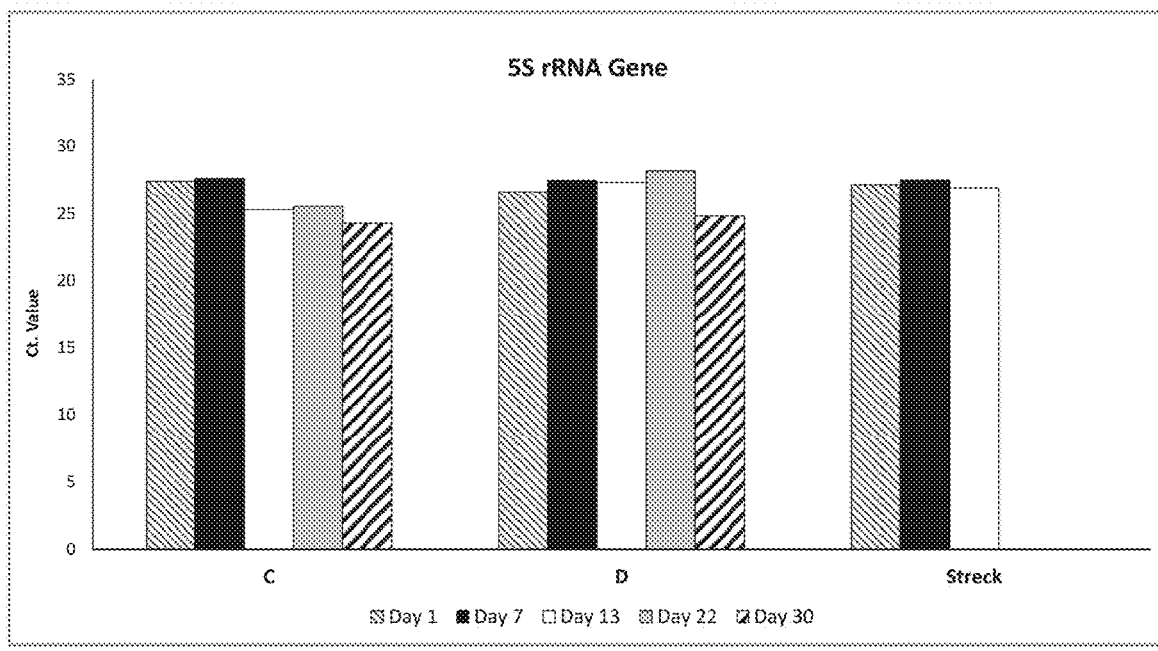
FIG. 5 is a graph showing the preservation of cfDNA in blood samples, stored for a period of up to 28 days, by detecting 5S rRNA using real time PCR. DNA was isolated from blood collected into: preservative tubes containing preservative compositions as disclosed herein (C; D) or a preservative tube containing a prior art preservative composition (Streck).

The Ct (cycle threshold) values generated from each time point and from the 3 different tubes were then summarized in Table 5. The Ct values were also plotted in FIG. 5. As shown in Table 5 and FIG. 5, Nucleic Acid Preservative C and Nucleic Acid Preservative D preserved the samples up to 30 days, as evidenced by the consistent Ct readings from day 1, day 7, day 13, day 22 and day 30. In contrast, it can be seen that the prior art Streck tubes resulted in extensive cell lysis after day 13, as the plasma could not be separated and the DNA could not be isolated. These results demonstrated that the Nucleic Acid Preservative C and Nucleic Acid Preservative D, provided enhanced long term preservation as compared to the prior art Streck tubes.

TABLE 5

| | | 5S Ct | | | | |
|---|---|---|---|---|---|---|
| Tube | Preservative | Day 1 | Day 7 | Day 13 | Day 22 | Day 30 |
| 1 | C | 27.4 | 27.6 | 25.3 | 25.56 | 24.31 |
| 2 | D | 26.61 | 27.46 | 27.32 | 28.18 | 24.84 |
| 3 | Streck Cell-Free DNA™ BCT | 27.14 | 27.5 | 26.9 | N/A | N/A |

Example 4— Improved Preservation of Male DNA Spiked into Female Blood Samples mL blood samples from a healthy male donor were drawn into 3 separate BD EDTA blood collection tubes (BD EDTA (K2) Tube Cat #366643; Becton Dickinson, Mississauga, Canada). The plasma was separated from each of the 3 blood samples by centrifugation for 15 minutes at 1000× g followed by transferring the plasma into a new 15 cc tube. The plasma was again centrifuged for 15 minutes at 1000× g and then transferred into a new 15 cc tube. The transferred plasma was further centrifuged for 15 minutes at 3000×g and then transferred into a new 15 cc tube. Finally, the recovered male donor plasma was centrifuged for an additional 15 minutes at 4000×g and then transferred into a new 15 cc tube. The male donor plasma recovered from all 3 blood samples were pooled together and mixed by gentle inversion.

Blood samples from two healthy female donors were drawn into 5 separate blood collection tubes containing Nucleic Acid Preservative A (Preservative A— Female Donor 1 and Preservative A— Female Donor 2) and into 5 separate Streck Cell-Free DNA™ BCT tubes (Streck— Female Donor 1 and Streck—Female Donor 2).

The blood collection tubes containing Nucleic Acid Preservative A (see Example 1) were BD plain blood collection tubes (BD Vacutainer® Serum Cat #366430; Becton Dickinson, Mississauga, Canada) containing approximately 1.5 mL of Nucleic Acid Preservative A. Each of the tubes was filled to contain approximately 9 mL of blood/Nucleic Acid Preservative A after blood collection.

Each of the Streck Cell-Free DNA™ BCT tubes (Catalog #218962; Streck, Omaha, USA) were filled to contain approximately 9 mL of blood/Streck preservative after blood collection.

Immediately after blood sample collection, all tubes were mixed by gentle inversion 10 times. All the blood samples collected from the two healthy female donors were spiked with 1 mL of the previously recovered male donor plasma. All tubes were mixed by gentle inversion. All 20 tubes were then stored at room temperature.

At each time point (day 0, day 7, day 14, day 21 and day 30), plasma was separated for both female donors from one each of the Nucleic Acid Preservative A tubes and the Streck tubes by centrifugation for 15 minutes at 1000× g followed by transferring the plasma into a new 15 cc tube. The plasma was then centrifuged for 15 minutes at 1000× g and then transferred into a new 15 cc tube. The transferred plasma was further centrifuged for 15 minutes at 3000× g and then transferred into a new 15 cc tube. Finally, the recovered plasma was centrifuged for an additional 15 minutes at 4000× g and then transferred into a new 15 cc tube. The plasma volume recovered from all tubes at each time point was recorded (Table 6). All plasma recovered from both female donors was stored at −70° C. until cfDNA isolation.

cfDNA was then isolated from the entirety of each plasma sample using Norgen's Plasma/Serum Cell-Free Circulating DNA Purification Midi Kit (Cat #55600, Norgen Biotek, Thorold, Canada) or using Norgen's Plasma/Serum Cell-Free Circulating DNA Purification Maxi Kit (Cat #55800, Norgen Biotek, Thorold, Canada) depending on the plasma sample volume shown below in Table 6 and according to the manufacturer's instructions.

TABLE 6

Volume of plasma recovered from blood samples-previously collected into a blood collection tube containing Nucleic Acid Preservative A or a Streck Cell-Free DNA™ BCT tube-from Female Donor 1 and Female Donor 2 at the different storage time points

| | | Plasma Volume (mL) | | | |
|---|---|---|---|---|---|
| | | Preservative A | | Streck DNA BCT Tube | |
| | | Female Donor 1 | Female Donor 2 | Female Donor 1 | Female Donor 2 |
| cfDNA Isolation Time | Day 0 | 6.5 | 6.5 | 5 | 5.5 |
| | Day 7 | 6 | 6 | 5 | 4 |
| | Day 14 | 6.5 | 6.5 | 4 | 5 |
| | Day 21 | 6 | 6 | 4 | 4 |
| | Day 30 | 6.5 | 6.5 | 4 | 4 |

Levels of total purified cell-free plasma DNA were analyzed using Real-Time PCR amplification of a 156 bp GAPDH gene, whereas levels of the spiked-in male DNA was analyzed using Real-Time PCR amplification of a 128 bp SRY gene. A consistent amount of the spiked-in male 128 bp SRY gene and a consistent amount of the total cfDNA, as represented by the 156 bp GAPDH gene, over the 30 day preservation period would indicate that both the male spiked-in DNA and the endogenous female cfDNA was being well preserved. An increase in the amount of the female cfDNA over time would indicate cell lysis and hence poor preservation. A decrease in the amount of the male spiked-in DNA would indicate either: 1) poor preservation due to degradation of the DNA or 2) that the male DNA has been masked by the leakage of the gDNA from the lysed cells, which will interfere with the detection of the male spiked-in DNA.

Further, a consistent percentage of the spiked-in male 128 bp SRY gene, as compared to the total DNA over the 30 day preservation period, would indicate that the DNA is being well preserved within the female plasma sample. A decrease in the percentage of the spiked-in male 128 bp SRY gene compared to the total DNA would indicate DNA degradation and hence poor preservation. A consistent amount of the 156 bp GAPDH gene during the 30 day preservation period would indicate that the female total cfDNA is being well preserved with no sign of cell lysis. An increase in the total amount of the 156 bp GAPDH gene would indicate that cell lysis is occurring.

The conditions of the real-time PCR were:
Real Time PCR Mix:
  5 µL of Plasma DNA
  10 µL Norgen's 2×PCR Master Mix (Cat #28007, Norgen Biotek, Thorold, Canada)
  0.4 µL GAPDH Primer Mix (25 µM)
  0.4 µL SRY Primer Mix (25 µM)
  0.2 µL GAPDH TaqMan Hex-Probe (25 µM)
  0.2 µL SRY TaqMan FAM-Probe (25 µM)
  3.8 µL Water
  20 µL PCR Reaction
Real-Time PCR Program:
  Cycle 1: (1×)
    Step 1:95.0° C. for 03:00
  Cycle 2: (40×)
    Step 95.0° C. for 00:15
    Step 60.0° C. for 00:30
  Data collection and real-time analysis enabled.

Figure 6:
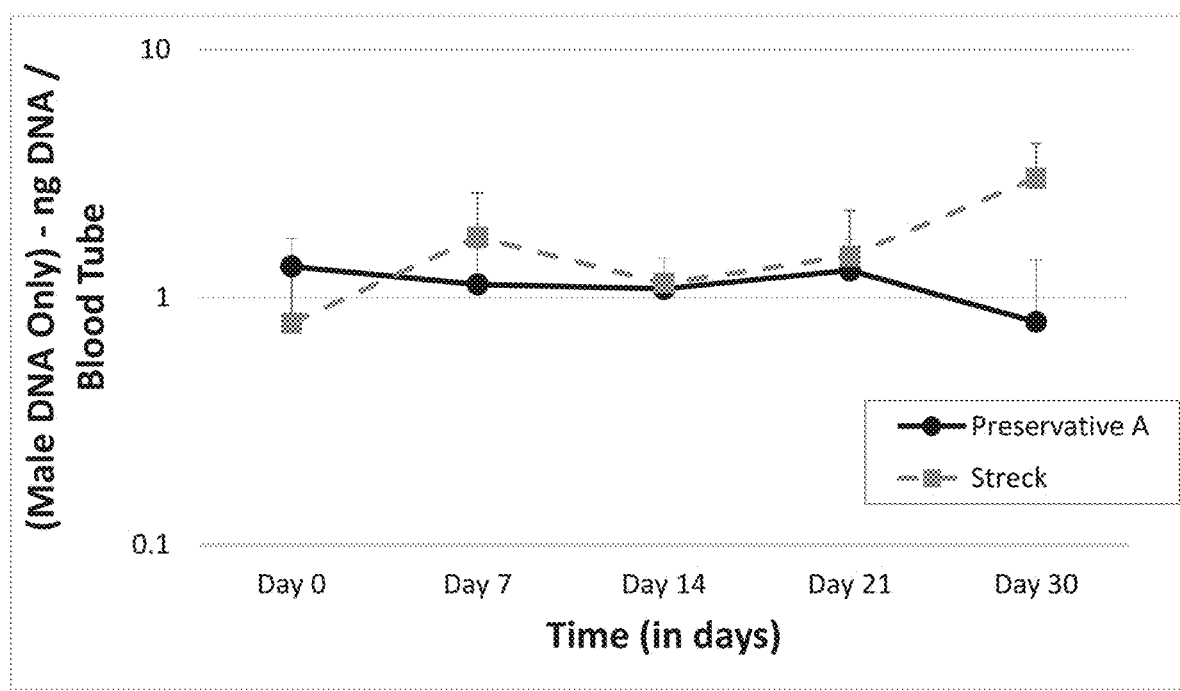
FIG. 6 is a graph showing the preservation of spiked-in male cfDNA in female blood samples, stored for a period of up to 30 days, by detecting the SRY gene using real time PCR.

The amount of the spiked-in male 128 bp SRY gene was plotted in FIG. 6. As shown in FIG. 6, Nucleic Acid Preservative A as well as Streck's DNA BCT tubes maintained a constant amount of the male spiked-in 128 bp SRY gene in the female plasma samples up to 30 days, as evidenced by the consistent amount of the male DNA from day 0, day 7, day 14, day 21 and day 30. This would indicate that the male spiked-in DNA did not degrade over time in both tubes.

Figure 7:
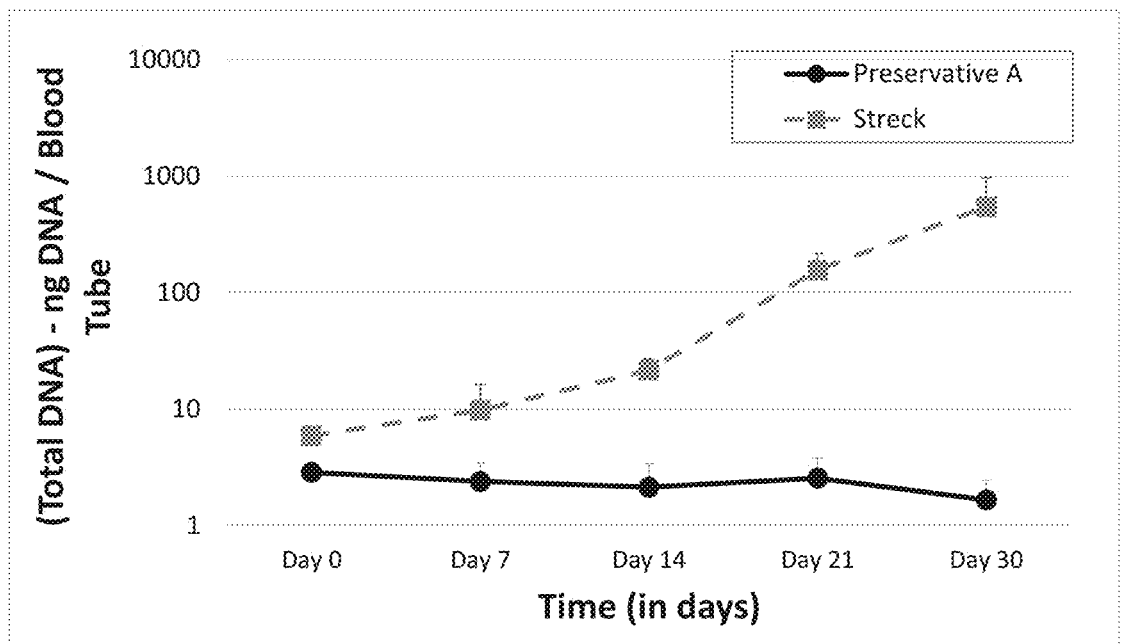
FIG. 7 is a graph showing the preservation of cfDNA in the female blood samples, by detecting the GAPDH gene using real time PCR.

The amount of the total DNA represented by the 156 bp GAPDH gene was plotted in FIG. 7. As shown in FIG. 7, Nucleic Acid Preservative A maintained a constant amount of the female 156 bp GAPDH gene up to 30 days, as evidenced by the consistent amount of the female total DNA measured at day 0, day 7, day 14, day 21 and day 30. As the amount of total DNA did not increase, this would indicate that there was no cell lysis in the samples stored in the tubes containing Nucleic Acid Preservative A. In contrast, sample storage in the prior art Streck tubes resulted in an increase in the amount of the total DNA past day 7, indicating poor sample preservation as evidenced by the release of gDNA in the female plasma.

Figure 8:
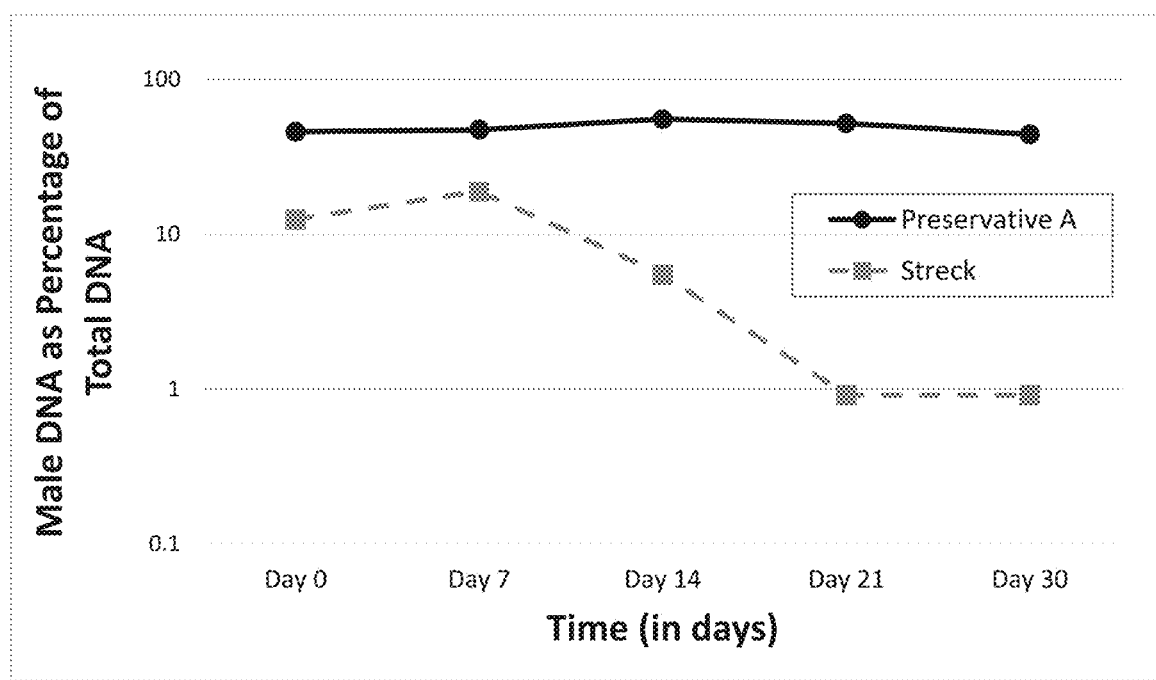
FIG. 8 is a graph showing the amount of detected SRY gene as a percentage of the total amount of female cfDNA. DNA was isolated from blood drawn from 2 different female individuals and collected into: a preservative tube containing a preservative composition as disclosed herein (A) and spiked with plasma from a male donor or a preservative tube containing a prior art preservative composition (Streck) and spiked with plasma from the male donor.

The amount of the spiked-in male 128 bp SRY gene as a percentage of the total female cfDNA was plotted in FIG. 8. As shown in FIG. 8, Nucleic Acid Preservative A maintained a constant amount of the male spiked-in 128 bp SRY gene in the female plasma samples up to 30 days, as evidenced by the consistent percentage of the male DNA to the total female cfDNA from day 0, day 7, day 14, day 21 and day 30. In contrast, storage in the prior art Streck tubes resulted in a decrease in the amount of the male DNA as a percentage of the total female cfDNA after day 7. These results demonstrated that Nucleic Acid Preservative A provided enhanced long term preservation of the 128 bp SRY-gene in plasma and prevented any cell lysis as compared to the prior art Streck preservative which resulted in lysis and the increase of total DNA over the 30 day period.

Example 5—Hemolysis of Collected Blood as Measured Over Time

Blood samples from three healthy donors were drawn into 5 separate blood collection tubes containing Nucleic Acid Preservative A (see Example 1), 5 separate Streck Cell-Free DNA™ BCT tubes, and 5 separate BD EDTA (K2) blood collection tubes.

The blood tubes containing Nucleic Acid Preservative A were BD plain blood collection tubes (BD Vacutainer® Serum Cat #366430; Becton Dickinson, Mississauga, Canada) containing approximately 1.5 mL of Nucleic Acid Preservative A. Each tube contained approximately 10 mL of blood/Nucleic Acid Preservative A after blood collection.

Each of the Streck Cell-Free DNA™ BCT tubes (Catalog #218962; Streck, Omaha, USA) contained approximately 10 mL of blood/Streck preservative after blood collection.

Each of the BD EDTA (K2) blood collection tubes (BD EDTC (K2) Tube Cat #366643; Becton Dickinson, Mississauga, Canada) contained approximately 10 mL of blood after blood collection.

All tubes were mixed by gentle inversion for 10 times and stored at room temperature for 30 days. The blood samples were processed at each time point starting at day 0, day 7, day 14, day 21 and day 30. Plasma was separated by centrifugation for 15 minutes at 450× g (2,000 RPM) followed by transferring the plasma into a new tube.

Figure 9:
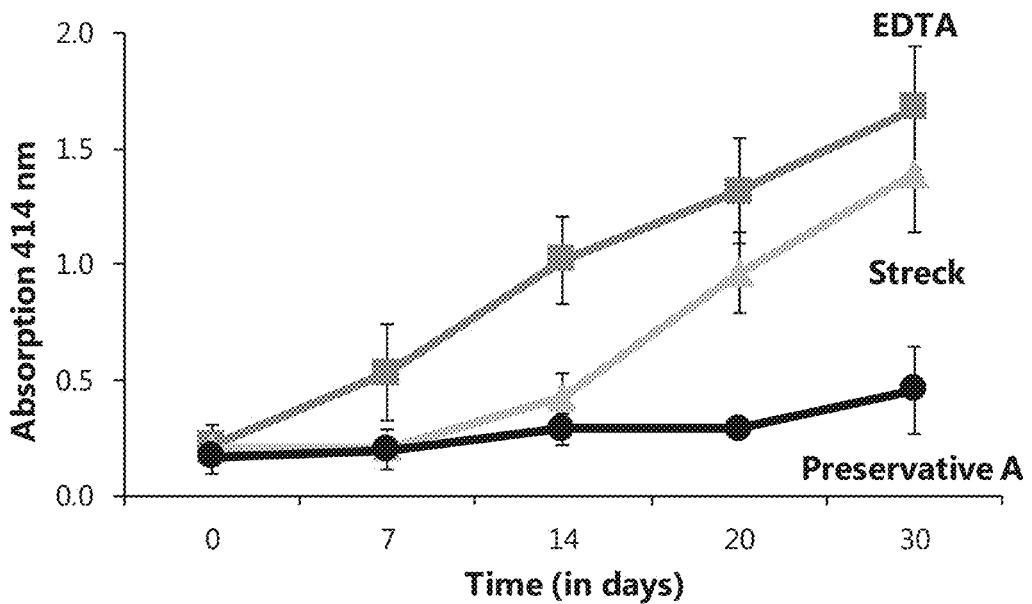
FIG. 9 is a graph comparing the amount of hemolysis in pooled blood samples, at individual storage time points (up to 30 days), as measured by the absorption of free hemoglobin at 414 nm. The blood samples were drawn from 3 different individuals and collected into: a preservative tube containing a preservative composition as disclosed herein (A); a preservative tube containing a prior art preservative composition (Streck) or a preservative tube containing EDTA (EDTA).

Hemolysis was determined by measuring the absorption of free hemoglobin in the recovered plasma from the 3 subjects at 414 nm over several time points using a Nanodrop 2000/2000c (Thermo Fisher Scientific, Ottawa, Canada). The separate 414 nm absorption values, for all time points, from the 3 different blood tubes are shown in FIG. 9 (averaged between the 3 donors at each time point). As shown in FIG. 9, plasma recovered from the tubes containing Nucleic Acid Preservative A maintained very low free hemoglobin levels over the entire 30 days of preservation at room temperature indicating superior preservation and cell lysis (hemolysis) prevention. Plasma recovered from Streck tubes started to show high free hemoglobin levels past day 14 indicating cell lysis and poor preservation, whereas plasma recovered from EDTA tubes started to show increases in free hemoglobin levels after day zero.

Example 6—Effect of Ambient Temperature Storage on Cell-Free Plasma DNA Preservation and gDNA Contamination Blood samples from three healthy donors were drawn into 5 separate blood collection tubes containing Nucleic Acid Preservative A (see Example 1), 5 separate Streck Cell-Free DNA™ BCT tubes and 5 separate BD EDTA (K2) blood collection tubes The blood tubes containing Nucleic Acid Preservative A were BD plain blood collection tubes (BD Vacutainer® Serum Cat #366430; Becton Dickinson, Mississauga, Canada) containing approximately 1.5 mL of Nucleic Acid Preservative A. Each tube contained approximately 10 mL of blood/Nucleic Acid Preservative A after blood collection.

Each of the Streck Cell-Free DNA™ BCT tubes (Catalog #218962; Streck, Omaha, USA) contained approximately 10 mL of blood/Streck preservative after blood collection.

Each of the BD EDTA (K2) blood collection tubes (BD EDTC (K2) Tube Cat #366643; Becton Dickinson, Mississauga, Canada) contained approximately 10 mL of blood after blood collection.

All tubes were mixed by gentle inversion 10 times and stored at room temperature for 30 days. The blood samples were processed at each time point starting at day 0, day 7, day 14, day 21 and day 30. The plasma from each blood sample was separated by centrifugation for 15 minutes at 450× g (~2,000 RPM) followed by transferring the plasma into a new tube. Cell-free plasma DNA was isolated from 0.5 ml from each plasma sample using Norgen's Plasma/Serum Cell-Free Circulating DNA Purification Mini Kit (Cat #55500, Norgen Biotek, Thorold, Canada) according to the manufacturer's instructions.

The purified cell-free plasma DNA was then analyzed using Real-Time PCR amplification of the Alu115 (representative of cfDNA) and Alu247 (representative of gDNA) gene targets. Amplification of the short ALU gene target (Alu115) and the long ALU gene target (Alu247) with a consistent Ct value would indicate that the cell-free plasma DNA is being preserved within the sample and that no cell lysis is occurring. A drop in the Ct value, especially for the long ALU gene (Alu247), would indicate cell lysis and consequently, gDNA contamination of the cell-free plasma DNA.

Real Time PCR Mix:
3 μL of Plasma DNA
10 μL Norgen's 2×PCR Master Mix (Cat #28007, Norgen Biotek, Thorold, Canada)
0.12 μL ALU Forward Primer (50 μM)
0.12 μL ALU Reverse Primer (50 μM)
0.03 μL 100× Syber Green Mix (Catalog #170-8880, BioRad, Hercules, USA)
6.73 μL Water
20 μL PCR Reaction Real-Time PCR Program:
Cycle 1: (1×)
  Step 1: 95.0° C. for 03:00
Cycle 2: (45×)
  Step 1: 95.0° C. for 00:30
  Step 2: 64.0° C. for 00:30
  Step 3: 72.0° C. for 00:30
  Data collection and real-time analysis enabled.
Cycle 3: (1×)
  Step 1: 57.0° C. for 01:00
Cycle 4: (80×)
  Step 1: 57.0° C. for 00:10
  Increase setpoint temperature after cycle 2 by 0.5° C.
  Melt curve data collection and analysis enabled.

Figure 10:
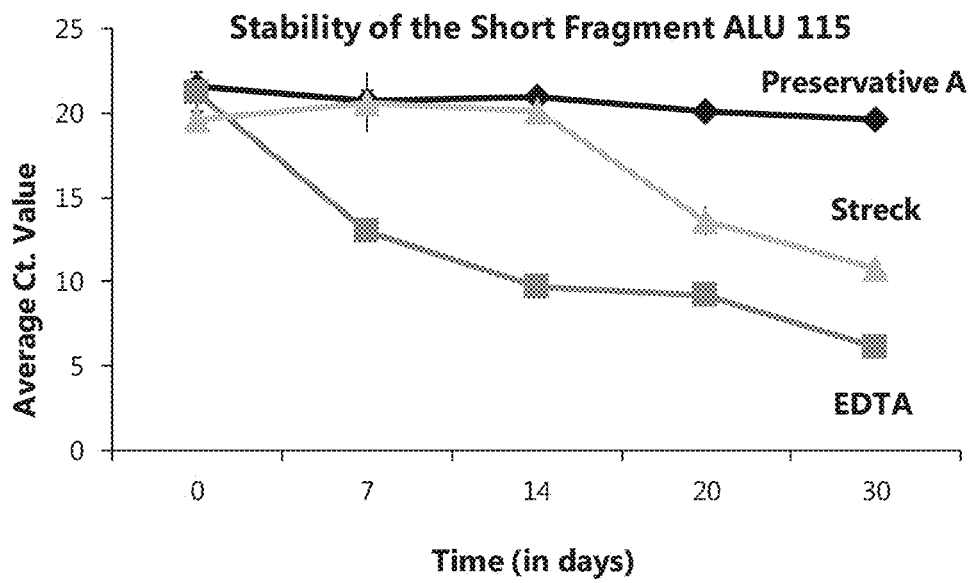
FIG. 10 is a graph showing the preservation of cfDNA in blood samples, stored for a period of up to 30 days at ambient temperature, by detecting Alu115 fragments using real time PCR.
Figure 11:
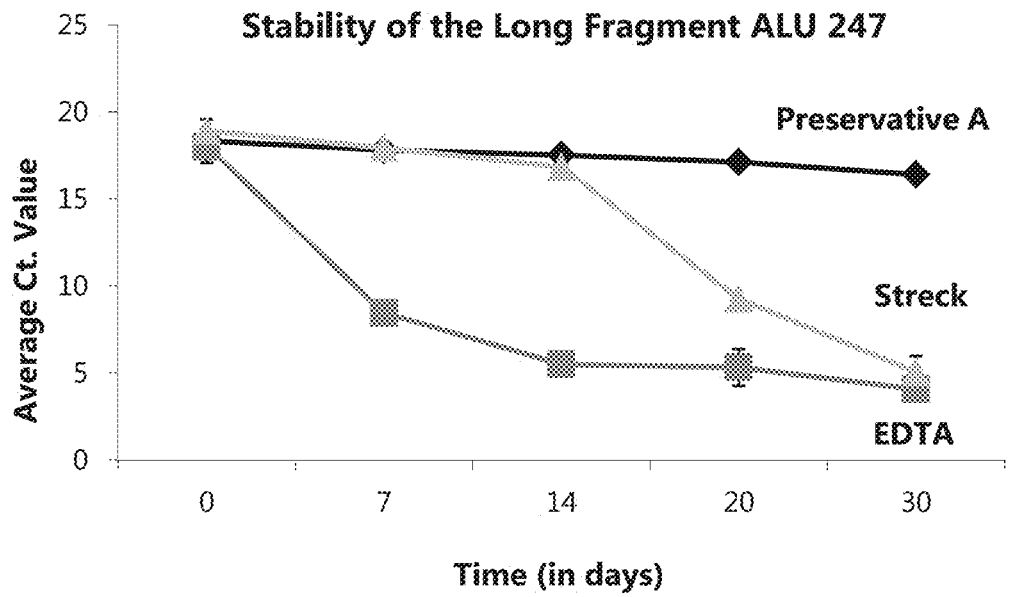
FIG. 11 is a graph showing the extent of gDNA contamination in the blood samples, stored for a period of up to 30 days at ambient temperature, by detecting Alu247 fragments using real time PCR. DNA was isolated from blood drawn from 3 different individuals and collected into: a preservative tube containing a preservative composition as disclosed herein (A), a preservative tube containing a prior art preservative composition (Streck) or a preservative tube containing EDTA (EDTA).

The average Ct (cycle threshold) values generated from the average of all 3 donors at each time point for the 3 different tubes were plotted in FIG. 10 (for Alu115) and in FIG. 11 (for Alu247). Nucleic Acid Preservative A preserved the samples up to 30 days, as evidenced by the consistent Ct readings for both the short ALU gene target (Alu115— FIG. 10) and the long ALU gene target (Alu247— FIG. 11) from day 0, day 7, day 14, day 21 and day 30. In contrast, storage in the prior art Streck tubes resulted in cell lysis after day 14, as evidenced by the significant decrease in the Ct values for both the short ALU gene target (Alu115— FIG. 10) and the long ALU gene target (Alu247— FIG. 11). As for the plasma recovered from the blood samples collected in the BD EDTA (K2) blood collection tubes, significant cell lysis has occurred after 1-2 days from blood collection, as evidenced by the significant decrease in the Ct values for both the short ALU gene target (Alu115— FIG. 11) and the long ALU gene target (Alu247— FIG. 11).

Example 7—Effect of High Temperature (37° C.) Storage for 8 Days on gDNA Contamination Blood samples from three healthy donors were drawn into 5 separate blood collection tubes containing Nucleic Acid Preservative A (see Example 1), 5 separate Streck Cell-Free DNA™ BCT tubes, and 5 separate BD EDTA (K2) blood collection tubes.

The blood tubes containing Nucleic Acid Preservative A were BD plain blood collection tubes (BD Vacutainer® Serum Cat #366430; Becton Dickinson, Mississauga, Canada) containing approximately 1.5 mL of Nucleic Acid Preservative A. Each of the tubes contained approximately 10 mL of blood/Nucleic Acid Preservative A after blood collection.

Each of the Streck Cell-Free DNA™ BCT tubes (Catalog #218962; Streck, Omaha, USA) contained approximately 10 mL of blood/Streck preservative after blood collection.

Each of the BD EDTA (K2) blood collection tubes (BD EDTC (K2) Tube Cat #366643; Becton Dickinson, Mississauga, Canada) contained approximately 10 mL of blood after blood collection.

All tubes were mixed by gentle inversion 10 times and stored at 37° C. for 8 days. The blood samples were processed at each time point starting at day 0, day 1, day 2, day 4 and day 8. The plasma was separated by centrifugation for 15 minutes at 450× g (2,000 RPM) followed by transferring the plasma into a new tube. Cell-free plasma DNA was isolated from 0.5 mL of each plasma sample, using Norgen's Plasma/Serum Cell-Free Circulating DNA Purification Mini Kit (Cat #55500, Norgen Biotek, Thorold, Canada).

The purified cell-free plasma DNA was then analyzed using Real-Time PCR amplification of the long ALU gene (Alu247) representing the gDNA. Amplification of the long ALU gene (Alu247) with a consistent Ct value would indicate that the cell-free plasma DNA is being preserved within the sample and that no cell lysis is occurring. A drop in the Ct value would indicate cell lysis and consequently, gDNA contamination of the cell-free plasma DNA.

The conditions of the real-time PCR were:
Real Time PCR Mix:
3 μL of Plasma DNA
10 μL Norgen's 2×PCR Master Mix (Cat #28007, Norgen Biotek, Thorold, Canada)
0.12 μL ALU Forward Primer (50 μM)
0.12 μL ALU Reverse Primer (50 μM)
0.03 μL 100× Syber Green Mix (Catalog #170-8880, BioRad, Hercules, USA)
6.73 μL Water
20 μL PCR Reaction Real-Time PCR Program:
Cycle 1: (1×)
  Step 1: 95.0° C. for 03:00
Cycle 2: (45×)
  Step 1: 95.0° C. for 00:30
  Step 2: 64.0° C. for 00:30
  Step 3: 72.0° C. for 00:30
  Data collection and real-time analysis enabled.

Cycle 3: (1×)
  Step 1: 57.0° C. for 01:00
Cycle 4: (80×)
  Step 1: 57.0° C. for 00:10
  Increase setpoint temperature after cycle 2 by 0.5° C.
  Melt curve data collection and analysis enabled.

Figure 12:
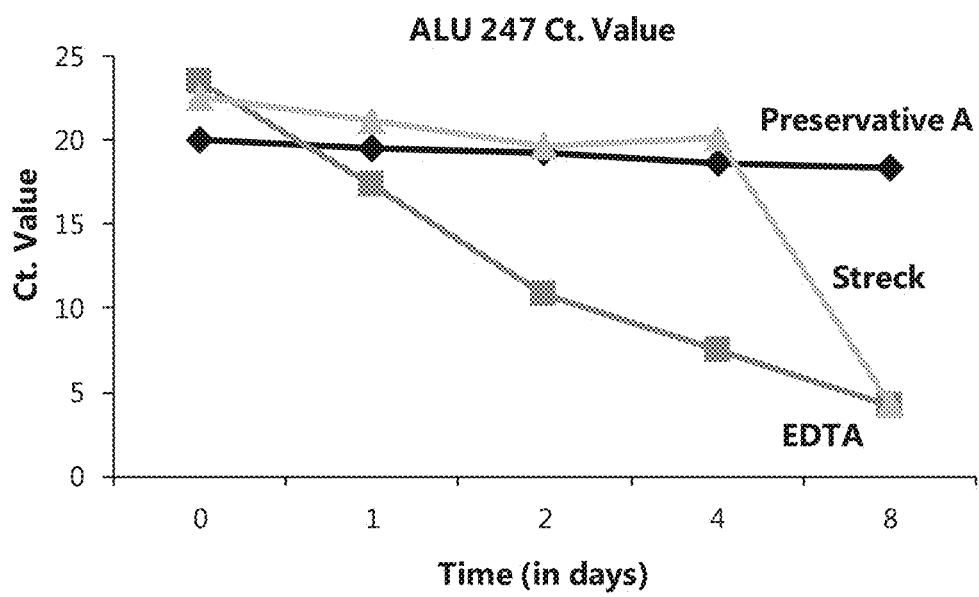
FIG. 12 is a showing graph showing the extent of gfDNA contamination in in blood samples, stored for a period of up to 8 days at 37° C., by detecting Alu247 fragments using real time PCR. DNA was isolated from blood from 3 different individuals, which was collected into: preservative tubes containing a preservative composition as disclosed herein (A), a preservative tube containing a prior art preservative composition (Streck) or a preservative tube containing EDTA (EDTA).

The average Ct (cycle threshold) values generated from the 3 donors at each time point and from the 3 different types of collection tubes were plotted in FIG. 12. Nucleic Acid Preservative A preserved the samples up to 8 days at 37° C., as evidenced by the consistent Ct readings for the long ALU gene target (Alu247) from day 0, day 1, day 2, day 4 and day 8. In contrast, storage in the prior art Streck tubes resulted in cell lysis after day 4, as evidenced by the significant decrease in the Ct values of the long ALU gene target (Alu247), which is indicative of cell lysis and gDNA leakage in the plasma. As for the plasma recovered from the BD EDTA (K2) blood collection tubes, significant cell lysis occurred a few hours after blood collection, as evidenced by the significant decrease in the Ct values for the long ALU gene target (Alu247) by day 1.

Example 8—Quality Assessment of Purified Cell-Free Plasma DNA Using the Agilent High Sensitivity DNA Kit Blood samples from a healthy female donor were drawn into 5 separate tubes containing Nucleic Acid Preservative A (see Example 1) and 5 separate Streck BCT DNA tubes.

The blood tubes containing Nucleic Acid Preservative A were BD plain blood collection tubes (BD Vacutainer® Serum Cat #366430; Becton Dickinson, Mississauga, Canada) containing approximately 1.5 mL of Nucleic Acid Preservative A. Each of the tubes contained approximately 10 mL of blood/Nucleic Acid Preservative A after blood collection.

Each of the Streck Cell-Free DNA™ BCT tubes (Catalog #218962; Streck, Omaha, USA) contained approximately 10 mL of blood/Streck preservative after blood collection.

Immediately after blood sample collection, all tubes were mixed by gentle inversion 10 times. At each time point (day 0, day 7, day 14, day 21 and day 30), plasma was separated from the tubes by centrifugation for 15 minutes at 1000× g followed by transferring the plasma into a new 15 cc tub. The plasma was then centrifuged for 15 minutes at 1000× g and then transferred into a new 15 cc tube. The transferred plasma was further centrifuged for 15 minutes at 3000× g then transferred into a new 15 cc tube. Finally, the recovered plasma was centrifuged for an additional 15 minutes at 4000× g and then transferred into a new 15 cc tube. The volume of the plasma recovered from all tubes, at each time point, was recorded in Table 7. All plasma recovered was stored at −70° C. until cfDNA isolation.

cfDNA was then isolated from the entire plasma sample using Norgen's Plasma/Serum Cell-Free Circulating DNA Purification Midi Kit (Cat #55600, Norgen Biotek, Thorold, Canada) or using Norgen's Plasma/Serum Cell-Free Circulating DNA Purification Maxi Kit (Cat #55800, Norgen Biotek, Thorold, Canada) depending on the plasma sample volume (see Table 7) and in accordance to the manufacturer's instructions.

TABLE 7

Volume of plasma recovered from blood samples-previously collected into a blood collection tube containing Nucleic Acid Preservative A or a Streck Cell-Free DNA™ BCT tube-from Female Donor 1 and Female Donor 2 at the different storage time points

| | | Plasma Volume (mL) | | | |
|---|---|---|---|---|---|
| | | Preservative A | | Streck DNA BCT Tube | |
| | | Female Donor 1 | Female Donor 2 | Female Donor 1 | Female Donor 2 |
| cfDNA Isolation Time | Day 0 | 6.5 | 6.5 | 5 | 5.5 |
| | Day 7 | 6 | 6 | 5 | 4 |
| | Day 14 | 6.5 | 6.5 | 4 | 5 |
| | Day 21 | 6 | 6 | 4 | 4 |
| | Day 30 | 6.5 | 6.5 | 4 | 4 |

The quality of the cell-free plasma DNA purified from plasma samples at each time point (day 0, day 7, day 14, day 21 and day 30) was assessed by analyzing 1 μL of the eluate was using the Agilent High Sensitivity DNA Kit (Cat #0.5067-4626, Aliglent Technologies, Santa Clara, USA). The appearance of a single nucleosome peak with a size range between 170-185 bp is representative of cfDNA normally found in plasma samples. The appearance of additional peaks with higher sizes than the previously mentioned nucleosome size range, would indicate the presence of apoptotic gDNA fragments resulting from cell lysis and therefore, would indicate poor sample preservation. Furthermore, a decrease in the size of the nucleosome peak at 170-185 bp, or a change in the distribution of the peak, would also indicate poor sample preservation due to DNA degradation or contamination with gDNA fragments.

Nucleic Acid Preservative A helped to prevent the release of high molecular weight gDNA into plasma, while also minimizing the accumulation of contaminating apoptotic ladder from dying peripheral blood leukocytes. As shown in Panels A, C, E, G, and I of FIG. 12, a single nucleosome peak (indicated by the solid circle) was maintained in the plasma recovered from the tubes containing Nucleic Acid Preservative A and stored at room temperature for 30 days. For these samples, there was no sign of gDNA contamination (e.g. the release of apoptotic DNA ladder). Therefore, the original cell-free DNA found within the plasma at time zero was maintained over the 30 day period with no degradation or contamination from gDNA. In contrast, as shown in Panels B, D, F, H and J of FIG. 12, storage at room temperature in the prior art Streck tubes resulted in cell lysis and the release of apoptotic DNA ladder (as indicated by the peaks in the dashed circle) after day 14, as well as the increase in the amount of DNA present in the original peak at 170-185 bp at time zero (as indicated by the solid circle).

Example 9— Preservation of Cell-Free Plasma DNA Up to 28 Days when Using Different Ratios of PEG to NaCl Five different variations of the preservative composition disclosed herein were prepared, each having a different PEG:NaCl ratio.

Nucleic Acid Preservative E comprised 25% w/w PEG; 7.5% w/w NaCl; 2% w/w EDTA; 0.023% w/w sodium azide and the balance, water. The PEG:NaCl ratio was about 3:1.

Nucleic Acid Preservative F comprised 26% w/w PEG; 6.5% w/w NaCl; 2% w/w EDTA; 0.023% w/w sodium azide and the balance, water. The PEG:NaCl ratio was about 4:1.

Nucleic Acid Preservative G comprised 27% w/w PEG; 5.5% w/w NaCl; 2% w/w EDTA; 0.023% w/w sodium azide and the balance, water. The PEG:NaCl ratio was about 5:1.

Nucleic Acid Preservative H comprised 28% w/w PEG; 4.5% w/w NaCl; 2% w/w EDTA; 0.023% w/w sodium azide and the balance, water. The PEG:NaCl ratio was about 6:1.

Nucleic Acid Preservative I comprised 29% w/w PEG; 3.5% w/w NaCl; 2% w/w EDTA; 0.023% w/w sodium azide and the balance, water. The PEG:NaCl ratio was about 8:1.

Blood samples from a single healthy donor were drawn into 5 separate blood collection tubes (Tubes 1-5).

Tube 1 was a BD plain blood collection tube (BD Vacutainer® Serum Cat #366430; Becton Dickinson, Mississauga, Canada) containing between 8 and 9 ml of blood and approximately 1.5-2 mL of Nucleic Acid Preservative E.

Tube 2 was a BD plain blood collection tube (BD Vacutainer® Serum Cat #366430; Becton Dickinson, Mississauga, Canada) containing between 8 and 9 ml of blood and approximately 1.5-2 mL of Nucleic Acid Preservative F.

Tube 3 was a BD plain blood collection tube (BD Vacutainer® Serum Cat #366430; Becton Dickinson, Mississauga, Canada) containing between 8 and 9 ml of blood and approximately 1.5-2 mL of Nucleic Acid Preservative G.

Tube 4 was a BD plain blood collection tube (BD Vacutainer® Serum Cat #366430; Becton Dickinson, Mississauga, Canada) containing between 8 and 9 ml of blood and approximately 1.5-2 mL of Nucleic Acid Preservative H.

Tube 5 was a BD plain blood collection tube (BD Vacutainer® Serum Cat #366430; Becton Dickinson, Mississauga, Canada) containing between 8 and 9 ml of blood and approximately 1.5-2 mL of Nucleic Acid Preservative I.

All tubes were mixed by inversion ten times after blood collection and placed at room temperature. Initial aliquots of preserved blood were removed from each tube to represent time zero, and aliquots of the preserved blood were removed from Tubes 1 to 5 after day 10 and day 28 for sampling. Plasma was separated by centrifugation for 15 minutes at 400× g (2,000 RPM) followed by transferring 1 mL of the plasma into a new tube. The recovered 1 mL plasma was divided into two 0.5 mL fractions, and the cell-free plasma DNA was then isolated from the duplicate 0.5 mL fractions using Norgen's Plasma/Serum Cell-Free Circulating DNA Purification Mini Kit (Cat #55100, Norgen Biotek, Thorold, Canada) according to the manufacturer's instructions.

Levels of total purified cell-free plasma DNA were analyzed using Real-Time PCR amplification of a 156 bp GAPDH gene target. The average Ct (cycle threshold) value was generated for each preservative tested and at each time point. A consistent Ct value would indicate a consistent amount of the total cfDNA, as represented by the GAPDH gene, in the plasma sample over the 28 day preservation period. A consistent Ct value would therefore, indicate that the cfDNA was being well preserved. If cell lysis had occurred during storage, then the total amount of cfDNA, as represented by the GAPDH gene, would increase over time and the Ct values would correspondingly decrease. An increase in the amount of total cfDNA over time would therefore, be indicative of poor sample preservation.

The conditions of the real-time PCR were:
Real Time PCR Mix:
  5 µL of Plasma DNA
  10 µL Norgen's 2×PCR Master Mix (Cat #28007, Norgen Biotek, Thorold, Canada)
  0.4 µL GAPDH Primer Mix (25 µM)
  0.2 µL GAPDH TaqMan Hex-Probe (25 µM)
  4.4 µL Water
  20 µL PCR Reaction Real-Time PCR Program:
  Cycle 1: (1×)
    Step 1: 95.0° C. for 03:00
  Cycle 2: (40×)
    Step 1: 95.0° C. for 00:15
    Step 2: 60.0° C. for 00:30
    Data collection and real-time analysis enabled.

Figure 14:
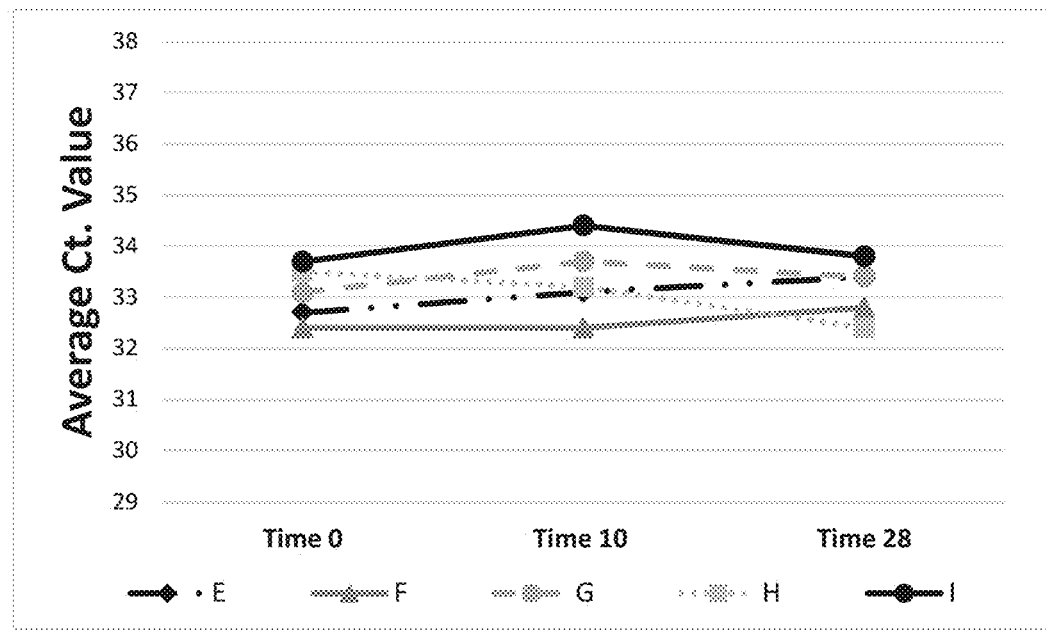
FIG. 14 is graph showing the preservation of cfDNA in blood samples, stored for a period of up to 30 days, by detecting the GAPDH gene using real time PCR. DNA was isolated from blood collected into a preservative tube comprising a preservative composition as disclosed herein (E, F, G, H or I).

The average Ct (cycle threshold) value generated from each preservative tested, at each time point, was determined and plotted in FIG. 14. As discussed above, if the total cfDNA in the sample has been preserved, then the Ct values will remain consistent over the 28 days. If the sample has not been preserved and cell lysis has occurred, then the amount of GAPDH would increase and the Ct values would decrease. As shown in FIG. 14, samples treated with each of the different preservatives having varying PEG:NaCl ratios, showed a constant amount of the GAPDH gene up to 28 days. These results showed that effective preservation can be achieved using a preservative composition as disclosed herein comprising PEG and NaCl at varying ratios.

Example 10— Preservation of Cell-Free Plasma DNA Up to 30 Days when Using Different PEG Derivatives Four different variations of Nucleic Acid Preservative A (see Example 1) were prepared using PEG 2000, PEG 4000, PEG 6000 or PEG 8000.

Blood samples from a single healthy donor were drawn into 4 separate blood collection tubes (Tubes 1-4).

Tube 1 was a BD plain blood collection tube (BD Vacutainer® Serum Cat #366430; Becton Dickinson, Mississauga, Canada) containing between 8 and 9 ml of blood and approximately 1.5-2 mL of the Nucleic Acid Preservative prepared with PEG 2000.

Tube 2 was a BD plain blood collection tube (BD Vacutainer® Serum Cat #366430; Becton Dickinson, Mississauga, Canada) containing between 8 and 9 ml of blood and approximately 1.5-2 mL of the Nucleic Acid Preservative prepared with PEG 4000.

Tube 3 was a BD plain blood collection tube (BD Vacutainer® Serum Cat #366430; Becton Dickinson, Mississauga, Canada) containing between 8 and 9 ml of blood and approximately 1.5-2 mL of the Nucleic Acid Preservative prepared with PEG 6000.

Tube 4 was a BD plain blood collection tube (BD Vacutainer® Serum Cat #366430; Becton Dickinson, Mississauga, Canada) containing between 8 and 9 ml of blood and approximately 1.5-2 mL of the Nucleic Acid Preservative prepared with PEG 8000.

All tubes were mixed by inversion ten times after blood collection and placed at room temperature. Initial aliquots of preserved blood were removed from each tube to represent time zero, and aliquots of the preserved blood were removed from Tubes 1 to 4 after day 10, day and day 30 for sampling. Plasma was separated by centrifugation for 15 minutes at 400× g (~2,000 RPM) followed by transferring 1 mL of the plasma into a new tube. The recovered 1 mL plasma was divided into two 0.5 mL fractions, and the cell-free DNA was then isolated from the duplicate 0.5 mL fractions from each time point using Norgen's Plasma/Serum Cell-Free Circulating DNA Purification Mini Kit (Cat #55100, Norgen Biotek, Thorold, Canada) according to the manufacturer's instructions.

Levels of total purified cell-free plasma DNA were analyzed using Real-Time PCR amplification of a 156 bp GAPDH gene. The average Ct (cycle threshold) value was generated from each preservative tested and at each time point. As previously noted, a constant Ct value would indicate a consistent amount of the total cfDNA, as represented by the GAPDH gene, over the 30 day preservation period. A consistent Ct value would therefore, indicate that the cfDNA was being well preserved. If cell lysis had occurred during storage, then the total amount of cfDNA, as represented by the GAPDH gene, would increase over time and the Ct values would correspondingly decrease. An increase in the amount of total cfDNA over time would therefore, be indicative of poor sample preservation.

The conditions of the real-time PCR were:
Real Time PCR Mix:
 5 µL of Plasma DNA
 10 µL Norgen's 2×PCR Master Mix (Cat #28007, Norgen Biotek, Thorold, Canada)
 0.4 µL GADPH Primer Mix (25 µM)
 0.2 µL GAPDH TaqMan Hex (25 µM)
 4.4 µL Water
 20 µL PCR Reaction
Real-Time PCR Program:
 Cycle 1: (1×)
  Step 1: 95.0° C. for 03:00
 Cycle 2: (40×)
  Step 1: 95.0° C. for 00:15
  Step 2: 60.0° C. for 00:30
 Data collection and real-time analysis enabled.

Figure 15:
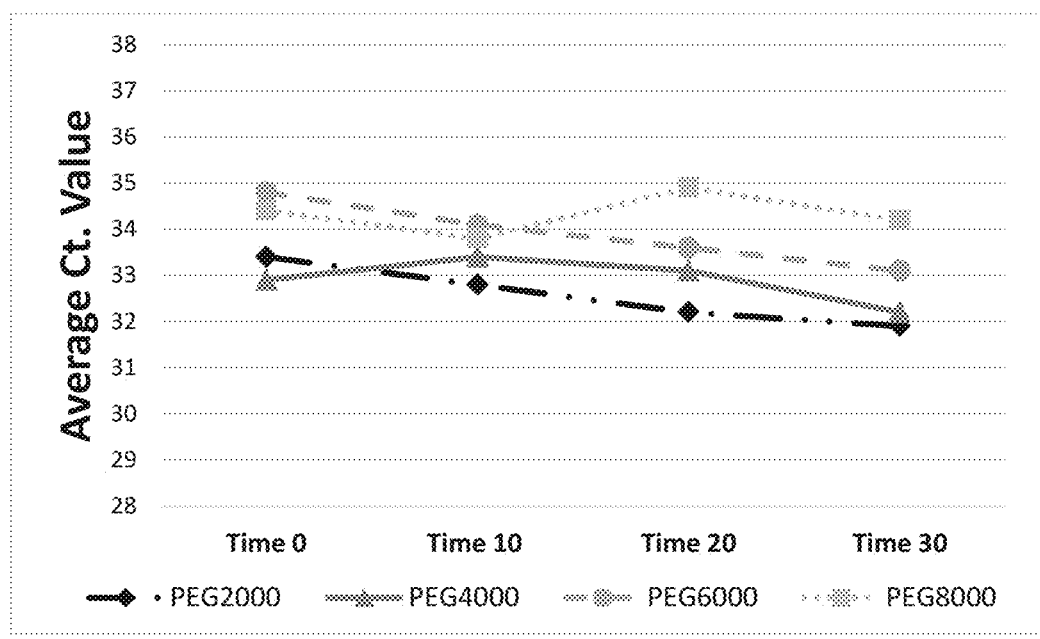
FIG. 15 is a graph showing the preservation of cfDNA in blood samples, stored for a period of up to 30 days, by detecting the GAPDH gene using real time PCR. DNA was isolated from blood collected into a preservative tube comprising a preservative composition as disclosed herein (A) prepared using PEG 2000, PEG 4000, PEG 6000 or PEG 8000.

The average Ct (cycle threshold) value generated from each preservative tested, at each time point, was determined and plotted in FIG. 15. As discussed above, if the cfDNA is being preserved then the Ct values will remain consistent over the 30 days. If cell lysis had occurred during storage, then the amount of GAPDH would increase over time and the Ct values would correspondingly decrease. As shown in FIG. 15, samples treated with each of the different preservatives containing different PEG derivatives, showed a constant amount of the GAPDH gene up to 30 days. These results showed that effective preservation can be achieved using a preservative composition as disclosed herein comprising PEG of varying molecular weight.

The invention claimed is:

1. A method for preserving nucleic acids and/or cells in a biological sample comprising the steps of:
 providing a composition comprising:
  at least one volume excluding polymer, wherein the at least one volume excluding polymer is polyethylene glycol (PEG) present in an amount of about 20 to about 40% by weight of the composition;
  at least one osmotic agent, wherein the at least one osmotic agent is NaCl present in an amount of about 1 to about 20% by weight of the composition;
  at least one enzyme inhibitor, wherein the at least one enzyme inhibitor is EDTA or citrate present in an amount from about 1 to about 30% by weight of the composition; and
  a metabolic inhibitor, wherein the metabolic inhibitor is sodium azide present in an amount from about 0.01 to about 10% by weight of the composition; and
 preventing or reducing the degradation of nucleic acids and/or cell lysis in the biological sample by contacting the biological sample with the composition to provide a treated sample.

2. The method according to claim 1, wherein the biological sample is a biological fluid and wherein the biological fluid is blood, plasma, serum, urine, saliva, stool, breast milk, tears, sweat, cerebralspinal fluid, synovial fluid, semen, vaginal fluid, ascitic fluid, amniotic fluid, or cell culture media.

3. The method of claim 2, wherein the biological fluid comprises tumour cells.

4. The method according to claim 1, wherein the nucleic acid is cell free RNA, cell free DNA or a combination thereof.

5. The method according to claim 1, wherein the treated sample is stored for a period of at least 1 day, at least 7 days, at least 14 days, at least 21 days, at least 28 days, or at least 40 days and optionally, at least a portion of the storage period occurs at ambient temperature.

6. The method according to claim 1, wherein the method is for preserving nucleic acids and further comprises the step of isolating the nucleic acids from the biological sample.

7. The method according to claim 6, wherein the isolated nucleic acids are used in a downstream analysis for diagnosing a disease or infection or for monitoring a disease or infection.

8. The method according to claim 1, wherein the at least one osmotic agent is NaCl present in an amount of about 1 to about 10% by weight of the composition.

9. The method according to claim 1, wherein the composition consists of
 at least one volume excluding polymer, wherein the at least one volume excluding polymer is polyethylene glycol (PEG) present in an amount of about 20 to about 40% by weight of the composition;
 at least one osmotic agent, wherein the at least one osmotic agent is NaCl present in an amount of about 1 to about 20% by weight of the composition;
 at least one nuclease inhibitor, wherein the at least one nuclease inhibitor is EDTA or citrate present in an amount from about 1 to about 10% by weight of the composition;
 a metabolic inhibitor, wherein the metabolic inhibitor is sodium azide present in an amount from about 0.01 to about 2% by weight of the composition; and
 the balance is water.

10. The method of claim 9, wherein the at least one osmotic agent is NaCl present in an amount of about 1 to about 10% by weight of the composition.

11. The method of claim 9, wherein the at least one volume excluding polymer is polyethylene glycol (PEG) present in an amount of about 33% by weight of the composition;
 the at least one osmotic agent is NaCl present in an amount of about 5% by weight of the composition;
 the at least one nuclease inhibitor is EDTA an amount of about 2% by weight of the composition;
 the metabolic inhibitor is sodium azide present in an amount of about 0.023% by weight of the composition; and
 the balance is water.

12. The method of claim 9, wherein the at least one volume excluding polymer is polyethylene glycol (PEG) present in an amount of about 25% by weight of the composition;
 the at least one osmotic agent is NaCl present in an amount of about 1 to about 10% by weight of the composition;
 the at least one nuclease inhibitor is EDTA an amount of about 3% by weight of the composition;
 the metabolic inhibitor is sodium azide present in an amount of about 0.033% by weight of the composition; and
 the balance is water.

13. The method of claim 9, wherein the at least one volume excluding polymer is polyethylene glycol (PEG) present in an amount of about 25% by weight of the composition;
- the at least one osmotic agent is NaCl present in an amount of about 3% by weight of the composition;
- the at least one nuclease inhibitor is EDTA an amount of about 3% by weight of the composition;
- the metabolic inhibitor is sodium azide present in an amount of about 0.033% by weight of the composition; and
- the balance is water.

* * * * *